US012691489B2

(12) United States Patent
Gifford, III et al.

(10) Patent No.: US 12,691,489 B2
(45) Date of Patent: Jul. 28, 2026

(54) EXPANDABLE DEVICES

(71) Applicant: The Foundry, LLC, Menlo Park, CA (US)

(72) Inventors: Hanson S. Gifford, III, Woodside, CA (US); Edward Dewitt Gifford, Glastonbury, CT (US); Vrad W. Levering, Smithville, TX (US)

(73) Assignee: The Foundry, LLC, Menlo Park, CA (US)

( * ) Notice: Subject to any disclaimer, the term of this patent is extended or adjusted under 35 U.S.C. 154(b) by 852 days.

(21) Appl. No.: 17/907,061

(22) PCT Filed: Mar. 24, 2021

(86) PCT No.: PCT/US2021/024020
§ 371 (c)(1),
(2) Date: Sep. 22, 2022

(87) PCT Pub. No.: WO2021/195305
PCT Pub. Date: Sep. 30, 2021

(65) Prior Publication Data
US 2023/0105665 A1    Apr. 6, 2023

Related U.S. Application Data

(60) Provisional application No. 62/993,876, filed on Mar. 24, 2020.

(51) Int. Cl.
*B21D 39/08* (2006.01)
*A61F 2/06* (2013.01)

(52) U.S. Cl.
CPC ................ *B21D 39/08* (2013.01); *A61F 2/06* (2013.01)

(58) Field of Classification Search
CPC ...... A61F 2002/825; A61F 2/06; A61F 2/958; A61F 2002/91575; A61F 2220/0091; A61F 2250/0039; A61F 2250/0048; A61F 2/915; B21D 39/08
See application file for complete search history.

(56) References Cited

U.S. PATENT DOCUMENTS 5,496,365 A      3/1996  Sgro
5,591,197 A  *  1/1997  Orth ........................ A61F 2/915
623/1.36

(Continued)

FOREIGN PATENT DOCUMENTS

CA          2634358 A1     6/2007
CN        101959478 A      1/2011

(Continued)

OTHER PUBLICATIONS

International Search Report and Written Opinion mailed Jul. 29, 2021; International Application No. PCT/US21/24020; 13 pages.

*Primary Examiner* — Tan-Uyen T Ho
(74) *Attorney, Agent, or Firm* — FORTEM IP LLP

(57) ABSTRACT

Expandable devices are disclosed herein. Several of the embodiments are directed towards an expandable device configured to be expanded within a conduit. The expandable device may comprise a tubular sidewall having first portions and second portions. Radial expansion of the expandable device may cause the first portions to bow outwardly and out of radial alignment with the second portions.

32 Claims, 12 Drawing Sheets

(56)                References Cited

U.S. PATENT DOCUMENTS

| | | | | |
|---|---|---|---|---|
| 5,681,346 A | * | 10/1997 | Orth | A61F 2/915 |
| | | | | 606/198 |
| 5,733,325 A | | 3/1998 | Robinson et al. | |
| 5,735,871 A | | 4/1998 | Sgro | |
| 5,853,419 A | | 12/1998 | Imran | |
| 6,206,910 B1 | | 3/2001 | Berry et al. | |
| 6,206,916 B1 | | 3/2001 | Furst | |
| 7,118,600 B2 | | 10/2006 | Dua et al. | |
| 7,815,673 B2 | * | 10/2010 | Bloom | A61F 2/915 |
| | | | | 623/1.15 |
| 8,114,152 B2 | | 2/2012 | Furst | |
| 8,696,729 B2 | | 4/2014 | Thompson et al. | |
| 8,894,702 B2 | | 11/2014 | Quadri et al. | |
| 10,238,339 B2 | * | 3/2019 | Dlugach | A61B 5/6876 |
| 10,470,881 B2 | | 11/2019 | Noe et al. | |
| 10,925,706 B2 | | 2/2021 | Eigler et al. | |
| 11,291,807 B2 | | 4/2022 | Eigler et al. | |
| 11,812,930 B2 | | 11/2023 | Jen et al. | |
| 11,850,138 B2 | | 12/2023 | Eigler et al. | |
| 2001/0011188 A1 | | 8/2001 | Berry et al. | |
| 2002/0052646 A1 | | 5/2002 | Fischell et al. | |
| 2002/0055767 A1 | | 5/2002 | Forde et al. | |
| 2003/0105517 A1 | | 6/2003 | White et al. | |
| 2005/0038501 A1 | | 2/2005 | Moore et al. | |
| 2005/0080478 A1 | | 4/2005 | Barongan | |
| 2007/0213813 A1 | | 9/2007 | Von et al. | |
| 2007/0239261 A1 | | 10/2007 | Bose et al. | |
| 2008/0077228 A1 | | 3/2008 | Goto | |
| 2008/0234800 A1 | | 9/2008 | Clarke | |
| 2009/0248132 A1 | | 10/2009 | Bloom et al. | |
| 2009/0248133 A1 | * | 10/2009 | Bloom | A61F 2/91 |
| | | | | 623/1.15 |
| 2009/0270972 A1 | | 10/2009 | Lane | |
| 2010/0174309 A1 | | 7/2010 | Fulkerson et al. | |
| 2011/0106234 A1 | | 5/2011 | Grandt | |
| 2011/0238154 A1 | | 9/2011 | Murphy et al. | |
| 2011/0251674 A1 | | 10/2011 | Schmid et al. | |
| 2012/0116498 A1 | | 5/2012 | Chuter et al. | |
| 2014/0180384 A1 | | 6/2014 | Leblanc et al. | |
| 2014/0200655 A1 | | 7/2014 | Webler et al. | |
| 2014/0277345 A1 | | 9/2014 | Havel et al. | |
| 2014/0277562 A1 | | 9/2014 | Seddon et al. | |

| | | | | |
|---|---|---|---|---|
| 2015/0216552 A1 | * | 8/2015 | Hefer | A61M 25/104 |
| | | | | 606/159 |
| 2015/0265438 A1 | | 9/2015 | Hossainy et al. | |
| 2016/0296327 A1 | | 10/2016 | Eberhardt et al. | |
| 2017/0172771 A1 | | 6/2017 | Bruckheimer et al. | |
| 2017/0231765 A1 | | 8/2017 | Desrosiers et al. | |
| 2017/0325948 A1 | | 11/2017 | Wallace et al. | |
| 2017/0340434 A1 | | 11/2017 | Cerchiari et al. | |
| 2017/0340460 A1 | | 11/2017 | Rosen et al. | |
| 2018/0206986 A1 | | 7/2018 | Noe et al. | |
| 2018/0344994 A1 | | 12/2018 | Karavany et al. | |
| 2019/0008628 A1 | | 1/2019 | Eigler et al. | |
| 2019/0110911 A1 | | 4/2019 | Nae et al. | |
| 2019/0175105 A1 | | 6/2019 | Dlugach et al. | |
| 2019/0262118 A1 | | 8/2019 | Eigler et al. | |
| 2019/0262129 A1 | | 8/2019 | Cooper et al. | |
| 2020/0229956 A1 | | 7/2020 | Jackson et al. | |
| 2020/0375721 A1 | | 12/2020 | Celermajer et al. | |
| 2021/0154032 A1 | | 5/2021 | Welch | |
| 2021/0161637 A1 | | 6/2021 | Eigler et al. | |
| 2021/0308433 A1 | | 10/2021 | Gifford, III et al. | |
| 2021/0353300 A1 | | 11/2021 | Kottenmeier et al. | |
| 2022/0175561 A1 | | 6/2022 | Doyle et al. | |
| 2022/0211492 A1 | | 7/2022 | Pintor et al. | |
| 2022/0346988 A1 | | 11/2022 | Okereke et al. | |
| 2023/0110800 A1 | | 4/2023 | Dienno, V | |
| 2023/0115137 A1 | | 4/2023 | Gifford et al. | |
| 2023/0118855 A1 | | 4/2023 | Gifford et al. | |
| 2023/0172757 A1 | | 6/2023 | Willner et al. | |
| 2023/0285172 A1 | | 9/2023 | King et al. | |
| 2024/0216135 A1 | | 7/2024 | Montorfano | |
| 2024/0261101 A1 | | 8/2024 | Mulligan et al. | |
| 2024/0398420 A1 | | 12/2024 | Dahan et al. | |

FOREIGN PATENT DOCUMENTS

| | | | |
|---|---|---|---|
| CN | 112618121 A | 4/2021 | |
| DE | 19653719 A1 | 4/1998 | |
| EP | 3248645 A1 | 11/2017 | |
| WO | 2018131043 A1 | 7/2018 | |
| WO | 2020033933 A1 | 2/2020 | |
| WO | 2020254835 A1 | 12/2020 | |
| WO | 2021195664 A1 | 9/2021 | |
| WO | 2021195665 A1 | 9/2021 | |
| WO | 2023091938 A1 | 5/2023 | |
| WO | 2023137000 A1 | 7/2023 | |

* cited by examiner

EXPANDABLE DEVICES

CROSS-REFERENCE TO RELATED APPLICATION(S)

The present application is a 371 U.S. national phase application of International Application No. PCT/US2021/024020, filed Mar. 24, 2021, which claims the benefit of priority to U.S. Patent Application No. 62/993,876, filed Mar. 24, 2020, which are incorporated herein by reference in their entireties.

SUMMARY

The expandable devices of the present technology include tubular sidewalls having portions configured to bow out of alignment with the rest of the sidewall as the device is expanded. The expandable devices of the present technology may have many applications, among which include construction, plumbing, oil pipelines, and others. The undulating topography of the expandable devices of the present technology may provide many benefits over conventional devices, as discussed herein. Among these benefits is the creation of an annular lumen that allows fluid flow past the expandable device while the expandable device is expanded within a conduit.

The subject technology is illustrated, for example, according to various aspects described below, including with reference to FIGS. 1A-8. Various examples of aspects of the subject technology are described as numbered clauses (1, 2, 3, etc.) for convenience. These are provided as examples and do not limit the subject technology.

1. An expandable device comprising:
    a tubular sidewall, the sidewall having first portions and second portions, wherein the expandable device has a collapsed configuration and an expanded configuration in which the expandable device is configured to be positioned within an opening at a target site,
    wherein transformation of the expandable device from the collapsed configuration to the expanded configuration causes the first portions of the sidewall to bow out of a cylindrical surface defined by the second portions of the sidewall such that, at least in the expanded configuration, the first portions form a plurality of buckled regions extending radially away from the second portions of the sidewall.

2. The expandable device of Clause 1, wherein the buckled regions are spaced apart about a circumference of the expandable device.

3. The expandable device of Clause 1 or Clause 2, wherein the buckled regions are spaced apart along a length of the expandable device.

4. The expandable device of any one of Clauses 1 to 3, wherein the buckled regions are disposed only at one or both of the first and second end portions of the expandable device.

5. The expandable device of any one of Clauses 1 to 3, wherein the buckled regions are disposed only along an intermediate portion of the expandable device.

6. The expandable device of any one of Clauses 1 to 5, wherein, when the expandable device is in a collapsed configuration, the first and second portions are generally radially aligned such that the sidewall has a substantially cylindrical surface.

7. The expandable device of any one of Clauses 1 to 6, wherein, when the expandable device is in an expanded configuration, the second portions are generally radially aligned along a length of the expandable device and the first portions are radially offset from the second portions.

8. The expandable device of any one of Clauses 1 to 7, wherein, when the expandable device is in an expanded configuration, at least some of the buckled regions extend radially outwardly from the second portions.

9. The expandable device of any one of Clauses 1 to 8, wherein, when the expandable device is in an expanded configuration, at least some of the buckled regions extend radially inwardly from the second portions.

10. The expandable device of any one of Clauses 1 to 9, wherein, when the expandable device is in an expanded configuration, the buckled regions comprise arched protrusions, and wherein each of the arched protrusions have (a) first and second end portions coupled to one of the second portions and (b) a peak region between the first and second end portions, the peak region comprising a portion of the buckled region that is radially farthest from the first and second end portions.

11. An expandable device comprising:
    a collapsed configuration and an expanded configuration in which the expandable device is configured to be positioned in a conduit,
    a plurality of spines and a plurality of struts, the spines extending along a longitudinal axis of the expandable device and the struts extending between circumferentially adjacent spines, each of the spines having first portions and second portions along a respective length of the spine, wherein:
        in the collapsed configuration, the struts and the spines are substantially the same radial distance from a central longitudinal axis of the expandable device and together define a substantially cylindrical surface surrounding a lumen, and
        in the expanded configuration, (a) the struts and the first portions of the spines are a first radial distance from the central longitudinal axis, and (b) the second portions of the spines are a second radial distance from the central longitudinal axis, the second radial distance different than the first radial distance.

12. The expandable device of Clause 11, wherein, when in the expanded configuration, the expandable device defines an annular lumen between (a) the second portions of the spines and (b) the struts and the first portions of the spines.

13. The expandable device of Clause 12, wherein, when the expandable device is in the expanded configuration, the struts and the first portions of the spines together define an expanded lumen through the expandable device, and wherein the annular lumen surrounds the expanded lumen.

14. The expandable device of Clause 12, wherein, when the expandable device is in the expanded configuration, the second portions of the expandable device together define an expanded lumen through the expandable device, and wherein the annular lumen surrounds the expanded lumen.

15. The expandable device of any one of Clauses 11 to 14, wherein the second radial distance is greater than the first radial distance.

16. The expandable device of any one of Clauses 11 to 15, wherein the second radial distance is less than the first radial distance.

17. The expandable device of any one of Clauses 11 to 16, wherein the second radial distance for some of the second portions is less than the first radial distance, and the second radial distance for others of the second portions is greater than the first radial distance.

18. The expandable device of any one of Clauses 11 to 17, wherein the spines are substantially linear in the collapsed configuration and have an undulating shape the expanded configuration.

19. An expandable device comprising:

a collapsed configuration and an expanded configuration in which the expandable device is configured to be positioned in a conduit, a plurality of spines and a plurality of struts, the spines extending along a longitudinal axis of the expandable device and the struts connecting adjacent spines, wherein:

the spines include a spine having first and second end portions, the struts include a first strut and a second strut— the first strut having first and second end portions, wherein the first end portion of the first strut is connected to the first end portion of the spine, the second strut having first and second end portions, wherein the second end portion of the second strut is connected to the second end portion of the spine, and wherein radial expansion of the expandable device decreases a longitudinal distance between the first end portion of the first strut and the second end portion of the second strut, and decreases a longitudinal distance between the first and second end portions of the spine, thereby causing the spine to buckle out of radial alignment with the first and second struts.

20. The expandable device of Clause 19, wherein the first and second struts are substantially linear in the collapsed configuration and in the expanded configuration.

21. The expandable device of Clause 20, wherein each of the first and second struts connect to the spine at flexible joints.

22. The expandable device of any one of Clauses 19 to 21, wherein the spine is longer than a combined length of the first and second struts.

23. The expandable device of any one of Clauses 19 to 22, wherein, when the expandable device is in the collapsed configuration, the first and second struts are substantially parallel to the spine.

24. The expandable device of any one of Clauses 19 to 23, wherein a second end terminus of the first strut and a first end terminus of the second strut are fixed relative to one another at a node.

25. The expandable device of Clause 24, wherein another one of the spines is coupled to the node.

26. The expandable device of Clause 24 or Clause 25, wherein the spine is a first spine and the expandable device further comprises a second spine having first and second end portions, a third strut having first and second end portions, and a fourth strut having first and second end portions, and wherein— the first end portion of the third strut is coupled to the first end portion of the second spine and the second end portion of the third strut is coupled to the node, the first end portion of the fourth strut is coupled to the node and the second end portion of the fourth strut is coupled to the second end portion of the second spine, and radial expansion of the expandable device decreases a longitudinal distance between the first end portion of the third strut and the second end portion of the fourth strut, and decreases a longitudinal distance between the first and second end portions of the second spine, thereby causing the second spine to buckle out of radial alignment with the third and fourth struts.

27. The expandable device of Clause 26, wherein, when the expandable device is in the collapsed configuration, the first, second, third, and fourth struts are substantially parallel to the first and second spines.

28. The expandable device of Clause 26 or Clause 27, wherein, when the expandable device is in the expanded configuration, the first, second, third and fourth struts angle away from the first and second spines, thereby forming an X where the node is at the intersection of the X.

29. The expandable device of any one of Clauses 26 to 28, wherein, when the expandable device is in an expanded configuration, the node, the first strut, the second strut, the third strut, and the fourth strut are substantially radially aligned at a first radial location and the first and second spines are radially offset from the first radial location and disposed at a second radial location.

30. The expandable device of any one of Clauses 26 to 29, wherein a second end terminus of the third strut and a first end terminus of the fourth strut are fixed relative to one another at the node.

31. The expandable device of any one of Clauses 24 to 30, further comprising a third spine running longitudinally through and coupled to the node.

32. The expandable device of any one of the previous Clauses, wherein the expandable device is configured to be expanded via expansion of an actuator positioned within a central lumen of the expandable device.

33. The expandable device of any one of the previous Clauses, wherein the expandable device is configured to be expanded within another expandable device.

34. The expandable device of any one of the previous Clauses, further comprising a valve coupled to the expandable device.

35. The expandable device of any one of the previous Clauses or of Clause 36, further comprising a tubular membrane bonded to at least some of the struts and/or spines defining the inner lumen of the expandable device.

36. The expandable device of any one of the previous Clauses, further comprising a tubular membrane bonded to at least some portions of some of the spines defining the outer lumen of the expandable device.

37. The expandable device of any one of the previous Clauses, wherein the expandable device comprises a super-elastic material.

38. The expandable device of any one of the previous Clauses, wherein the connections between at least some of the struts and spines are hinges.

39. The expandable device of any one of the previous Clauses, wherein the expandable device has been heat set at an intermediate expanded configuration, the intermediate expanded configuration having a diameter between a diameter of the expandable device in the collapsed configuration and a diameter of the expandable device in a fully expanded configuration.

40. The expandable device of any one of the previous Clauses, wherein the expandable device has been heat set at a fully expanded configuration.

41. The expandable device of any one of the previous Clauses, wherein the expandable device comprises a material that has been heat set.

42. The expandable device of any one of the previous Clauses, wherein the conduit is a pipe.

43. The expandable device of any one of the previous Clauses, wherein the conduit is configured to receive petroleum therethrough.

44. The expandable device of any one of the previous Clauses, wherein the conduit is a tubular support structure.

45. The expandable device of any one of the previous Clauses, wherein the conduit is an opening in a wall.

46. The expandable device of any one of the previous Clauses, wherein the conduit is an opening in a support structure.

47. A method for expanding an expandable device, the expandable device comprising a sidewall formed of a plurality of interconnected structural members including first connectors and second connectors, the second connectors extending between the first connectors, the method comprising:

> increasing an arc length between circumferentially adjacent first connectors, thereby decreasing a longitudinal distance between first ends of longitudinally adjacent second connectors and increasing a circumferential distance between second ends of the longitudinally adjacent second connectors, wherein the first ends of the longitudinally adjacent second connectors are coupled to a same one of the first connectors, and wherein the same one of the first connectors comprises a buckling region between the first ends of the longitudinally adjacent second connectors;
>
> longitudinally compressing the first connectors by decreasing the longitudinal distance between the first ends of the longitudinally adjacent second connectors; and
>
> forcing the buckling regions of the first connectors to bow out of radial alignment with the second connectors and other regions of the first connectors, thereby forming arched protrusions along the sidewall of the expandable device.

48. The method of Clause 44, further comprising positioning the expandable device in a conduit in a collapsed configuration, and wherein—

> when the expandable device is in the collapsed configuration, the first and second connectors together define a main lumen of the expandable device, and wherein the method further comprises (a) actuating an actuator within the main lumen to expand the expandable device within the conduit, thereby substantially blocking fluid flow through the main lumen of the expandable device, and (b) creating an annular lumen around the main lumen, thereby allowing fluid flow through the annular lumen while the actuator is blocking fluid flow through the main lumen.

49. The method of any one of the previous Clauses, wherein, when the expandable device is in a collapsed configuration, the first and second connectors together define a main lumen of the expandable device, wherein the method further comprises expanding an actuator within the main lumen to increase the circumferential arc length between adjacent first connectors.

50. The method of any one of the previous Clauses, further comprising creating an annular lumen between (a) portions of the arched protrusions that are radially farthest from the central longitudinal axis of the expandable device and (b) the second connectors and other regions of the first connectors.

51. The method of any one of the previous Clauses, wherein, when the expandable device is in a collapsed configuration, the first and second connectors are substantially the same radial distance from a central longitudinal axis of the expandable device and together define a main lumen of the expandable device.

52. The method of any one of the previous Clauses, wherein, when the expandable device is in the expanded configuration, (a) the second connectors and the other regions of the first connectors are a first radial distance from the central longitudinal axis, and (b) the buckling regions of the first connectors are a second radial distance from the central longitudinal axis different than the first radial distance.

53. The method of any one of the previous Clauses, wherein the expandable device is configured to be expanded within another expandable device.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figures 1A, 1B:
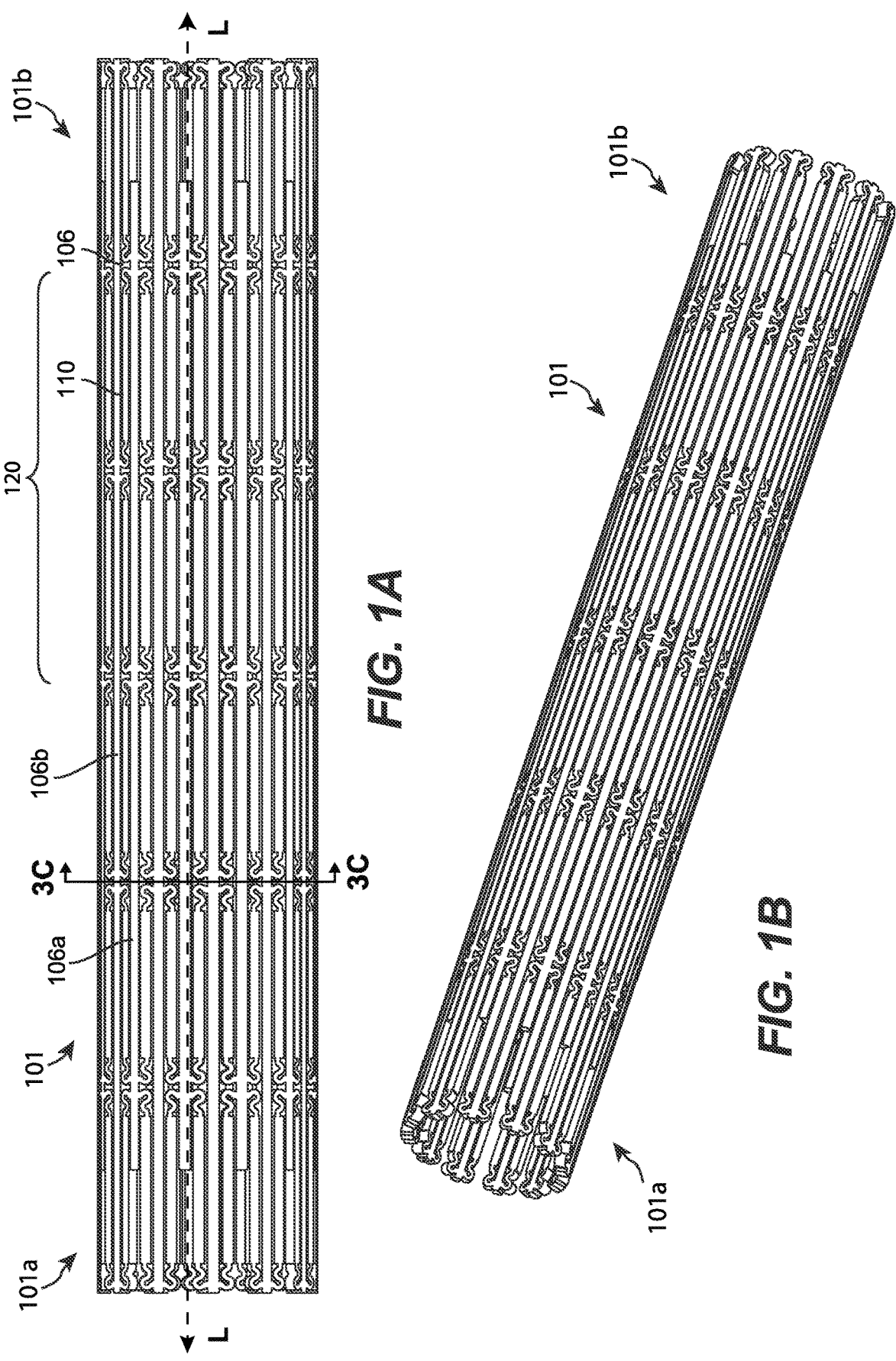
FIG. 1A is a side view of an expandable device in a tubular configuration configured in accordance with embodiments of the present technology.
FIG. 1B is an isometric view of the expandable device shown in FIG. 1A.

The present technology relates to expandable devices configured to be positioned within a conduit. Specific details of several embodiments of the technology are described below with reference to FIGS. 1A-8.

I. Definitions

As used herein, the "collapsed configuration" refers to an unexpanded configuration of the expandable device in which the expandable device is configured to be initially positioned at a target site. As used herein, the "expanded configuration" refers to a configuration of the expandable device in which the expandable element is partially or fully expanded. An expanded configuration may be achieved via actuation only (for example, via an actuating element), via self-expansion only, or both. In some embodiments, the expandable device may comprise a superelastic material and/or may be heat set to a desired shape, but the superelastic and/or heat set properties play a negligible role in expanding the expandable device. Unless provided otherwise herein, "fully expanded," as used to describe a configuration of the expandable device, and/or a cross-sectional dimension of the expandable device, refers to a configuration of the expandable device at a desired location. As used herein, "intermediate expanded configuration" refers to a configuration of the expandable device in between the collapsed configuration and the fully expanded configuration.

As used herein, the term "longitudinal" refers to a direction along an axis that extends through the lumen of the expandable device while in a tubular configuration, and the term "circumferential" can refer to a direction within a plane that is orthogonal to the longitudinal axis and extends around the circumference of the expandable device when in a tubular configuration.

As used herein, the terms "generally," "substantially," "about," and similar terms are used as terms of approximation and not as terms of degree, and are intended to account for the inherent variations in measured or calculated values that would be recognized by those of ordinary skill in the art.

As used herein, "conduit" and "flow passage" refer to any structure into or through which a fluid may flow. A conduit or flow passage may describe an open structure (i.e., having openings at both ends), or a closed structure (i.e., having an open end and a closed end).

II. Expandable Devices of the Present Technology

According to several aspects of the technology, the expandable devices disclosed herein comprise a tubular sidewall configured to be positioned within a conduit. Radial expansion of the expandable device causes portions of the sidewall to buckle out of the cylindrical surface defined by the non-buckling portions of the sidewall. The buckled portions thus form a plurality of bumps or arched protrusions extending radially inwardly and/or outwardly from the sidewall, which provide the expandable device with several benefits over existing devices. For example, the buckled portions can create an annular flow region around the main lumen of the expandable device that provides an alternative flow passage when an occlusive object (such as the actuator of the expandable member) is positioned within and occluding the main lumen. In these and other applications, the buckled portions may serve as frictional elements that engage apposing material at the expansion site to secure the expandable device at a desired location and limit migration. These and other applications of the present technology and the attendant advantages will be discussed in greater detail herein.

Figure 1C:
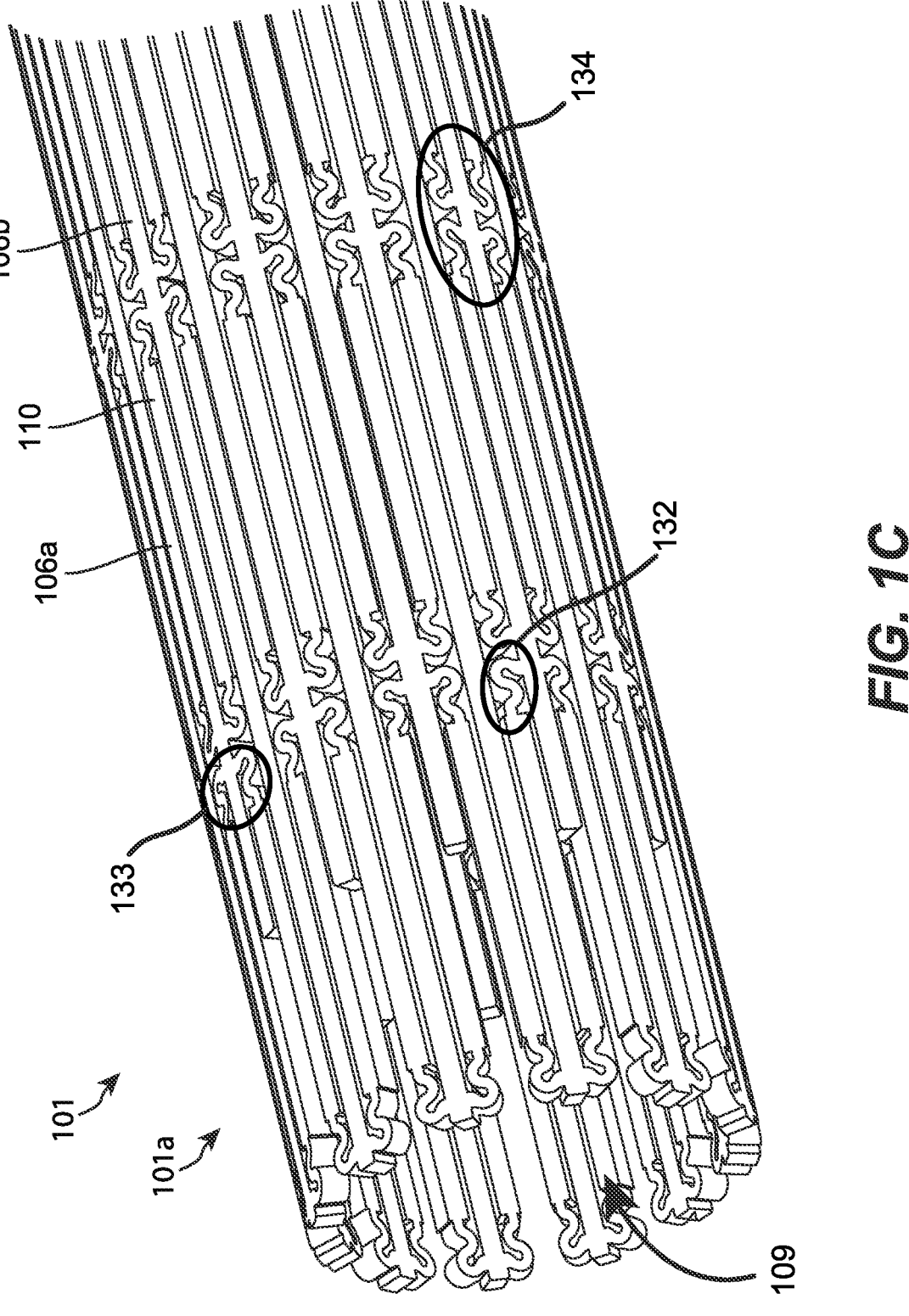
FIG. 1C is an enlarged, isometric view of a portion of the expandable device shown in FIGS. 1A and 1B.
Figure 1D:
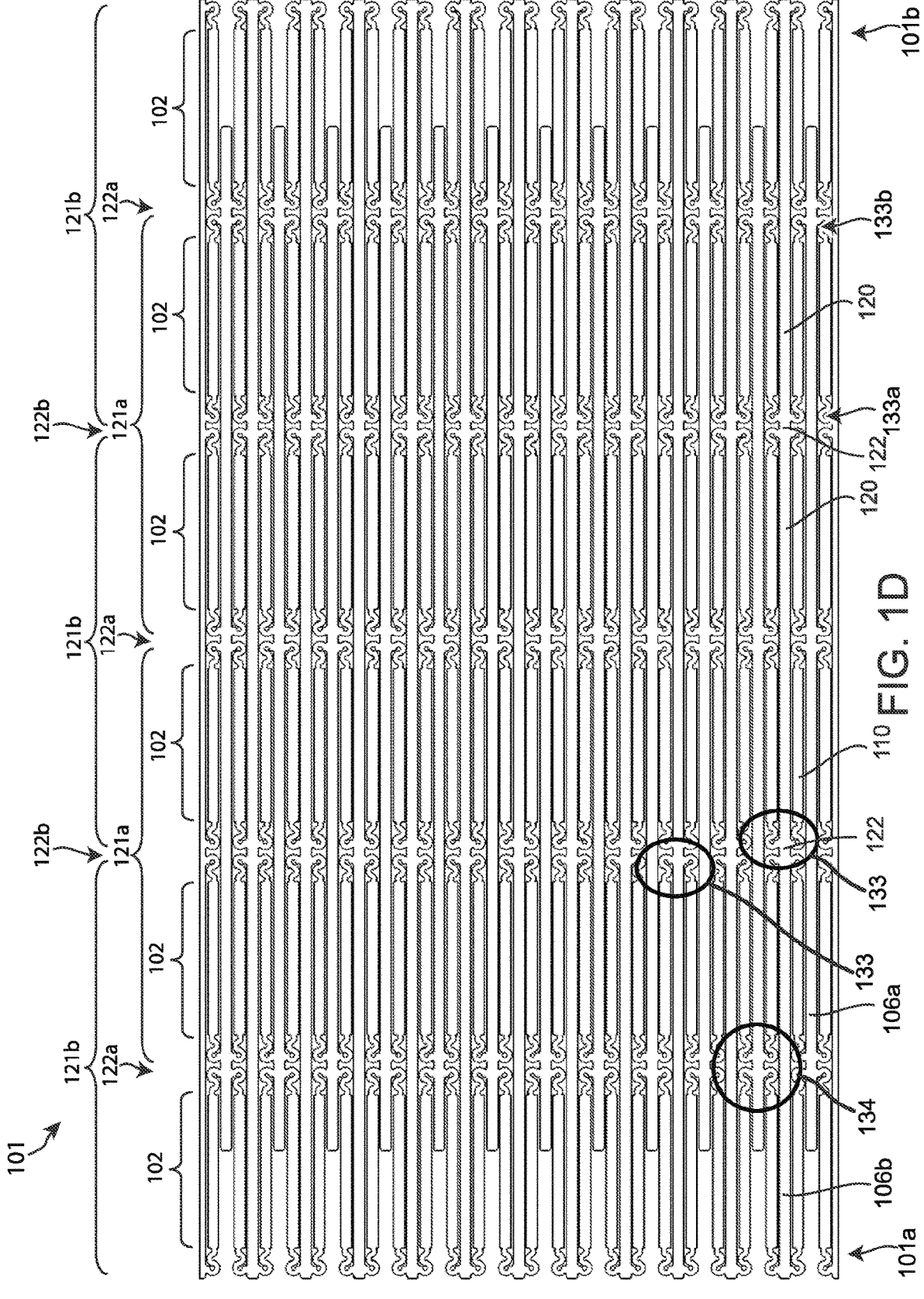
FIG. 1D is an elevation view of the expandable device shown in FIGS. 1A-1C in a laid flat configuration.

FIGS. 1A-1D illustrate an expandable device 101 configured in accordance with several embodiments of the present technology. FIGS. 1A-1C show the expandable device 101 in a collapsed (i.e., unexpanded), tubular configuration, and FIG. 1D shows the expandable device 101 as it would appear if, while in the collapsed configuration, it was cut longitudinally and then laid flat. When the expandable device 101 is described in a "laid flat" configuration, it should be assumed that the expandable device 101 is not under any compressive or tensile forces.

The expandable device 101 is configured to be delivered in the collapsed, tubular configuration to a target site within a conduit and radially expanded at the target site. The expandable device 101 may comprise a first end portion 101a, a second end portion 101b, and a length extending between the first and second end portions 101a, 101b along a longitudinal axis L (see FIG. 1A) of the expandable device 101. The expandable device 101 may comprise a tubular sidewall formed of a plurality of longitudinally-extending spines 106 and a plurality of struts 110 extending between circumferentially adjacent spines 106. As detailed herein, the spines 106 may include one or more first portions 120 configured to bow outwardly from the sidewall of the expandable device 101 when the expandable device 101 is in an expanded configuration.

According to some embodiments, for example as shown in FIGS. 1A-1D, each of the spines 106 may be connected to an adjacent spine 106 via one or more of the struts 110. For example, each of the struts 110 can have a first end portion coupled to a first one of the spines 106 and a second end portion coupled to a second one of the spines 106. As such, some or all of the struts 110 may extend between spines 106 and may not directly connect to another strut 110. In some embodiments, some or all of the struts 110 may extend between circumferentially adjacent spines 106 such that the spines and struts alternate about a circumference of the expandable device.

The end portions of the struts 110 may be coupled to the spines 106 via joints 132. The joints 132 may correspond to the first and second end portions of the struts 110, or may extend from the first and second end portions of the struts 110. The joints 132 can have a width, thickness, and shape designed to allow the struts 110 to swing away from the adjacent spines 106 as the device 100 radially expands, as well as to withstand the tension exerted on the struts 110 by the spines 106 as the spines 106 move away from one another during expansion. In some embodiments, the joints may be actual hinges rather than depending upon elastic or plastic deformation of material. In some embodiments, the expandable device 101 can include one or more spines 106 that are not connected to another spine 106 by a strut 110 and/or one or more spines 106 that are not connected to a strut 110.

According to some embodiments, for example as shown in FIGS. 1A-1D, some of the spines 106 may span only a portion of the length of the expandable device 101, while the other spines 106 may span the entire length of the expandable device 101. Likewise, one, some, or all of the spines 106 may have the same length, and one, some, or all of the spines 106 may have different lengths. As depicted, the expandable device 101 may include first spines 106a and second spines 106b that alternate about the circumference of the expandable device 101, where the first spines 106a are shorter than the second spines 106b. In some embodiments, the first and second spines 106a, 106b have the same length.

In some embodiments, the first end of one, some, or all of the struts 110 is coupled to one of the first spines 106a, and the second end of the strut(s) 110 may be coupled to one of the second spines 106b. The longer second spines 106b may extend longitudinally beyond one or both longitudinal ends of the first spines 106a, as shown, or a longitudinal end of the second spines 106b may be aligned with a longitudinal end of the first spines 106a. In some embodiments, no first spine 106a is circumferentially adjacent another first spine 106a and no second spine 106b is circumferentially adjacent another second spine 106b. In some embodiments, two or more first spines 106a may be circumferentially adjacent and/or two or more second spines 106b may be circumferentially adjacent.

At least when the expandable device is represented in a laid-flat view, for example as shown in FIG. 1D, one, some, or all of the spines 106 may be generally linear and substantially parallel to: (a) the longitudinal axis L of the expandable device 101, (b) one, some, or all of the struts 110, and/or (c) one, some, or all of the other spines 106. In these and other embodiments, when the expandable device 101 is in the collapsed configuration, one, some, or all of the spines 106 may be generally linear and substantially parallel to: (a) the longitudinal axis L, (b) one, some, or all of the struts 110, and/or (c) one, some, or all of the other spines 106.

Some or all of the struts 110 may be generally linear, as shown in FIGS. 1A-1D. At least when the expandable device is represented in a laid-flat view, for example as shown in FIG. 1D, the struts 110 may be generally linear and substantially parallel to: (a) the longitudinal axis L, (b) one, some, or all of the spines 106, and/or (c) the other struts 110 within the same strut region 102 and/or some or all of the other strut regions. In these and other embodiments, when the expandable device 101 is in the collapsed configuration, the struts 110 may be generally linear and substantially parallel to: (a) the longitudinal axis L, (b) one, some, or all of the spines 106, and/or (c) the other struts 110 within the same strut region 102 and/or some or all of the other strut regions. According to some embodiments, the struts 110 may be generally linear and angled relative to the longitudinal axis L and/or angled with respect to one, some, or all of the spines 106 when the expandable device is in an expanded configuration. In some embodiments, all or a portion of one or more of the struts 110 may be curved when the expandable device 101 is in a collapsed configuration and/or when the expandable device 101 is in an expanded configuration.

As best shown in FIG. 1D, the expandable device 101 may comprise a plurality of strut regions 102, each comprising a circumferential band of struts 110 within which adjacent struts 110 are separated by a coextending length of a spine 106. Each of the strut regions 102 may be longitudinally disposed between the first and second end portions of the struts 110 within the region 102 (and, similarly, between the joints 132 at the end portions of the struts 110 within region 102). At least when the expandable device 101 is in a collapsed configuration, the first end portions of the struts 110 within a given strut region 102 may be longitudinally aligned with one another and the second end portions of the struts 110 within a given strut region 102 may be longitudinally aligned with one another.

According to some embodiments, a first longitudinal side of each of the strut regions 102 may be defined by a circumferential band composed of first pairs 133a of joints 132 facing towards the second end portion 101b of the expandable device 101 (i.e., the struts 110 attached to the joints 132 of the first pairs 133a form a V-shape that opens in the direction of the second end portion 101b), and a second longitudinal side of each of the strut regions 102 may be defined by a circumferential band composed of second pairs 133b of joints 132 facing towards the first end portion 101a of the expandable device 101 (i.e., the struts 110 attached to the joints 132 of the second pairs 133b form a V-shape that opens in the direction of the first end portion 101a). The first pairs 133a of joints may be disposed along the first spines 106a and the second pairs 133b of joints may be disposed along the second spines 106b.

The strut regions 102 may be longitudinally adjacent one another along the length of the expandable device 101 such that the band of first pairs 133a of joints 132 of a first one of the strut regions 102 may be longitudinally adjacent the band of second pairs 133b of joints 132 of a longitudinally adjacent second strut region 102. The spines 106 may extend longitudinally across two or more strut regions 102, and thus at least some of the first pairs 133a are coupled to the second pairs 133b via a second portion 122 (described below) of the respective spine 106 along which the pairs 133a, 133b are disposed. First and second pairs 133a, 133b of joints that are longitudinally adjacent and radially aligned may comprise nodes 134.

According to some embodiments, for example as shown in FIG. 1D, one, some, or all of the spines 106 may comprise first portions 120 and second portions 122 that alternate along the lengths of the respective spines 106. First and second end portions 120a and 120b (see FIG. 2B) of the first portions 120 may be coupled to and continuous with one of the second portions 122. The first portions 120 may span one, two, or more strut regions 102, and the second portions 122 may extend between longitudinally adjacent strut regions 102 and between longitudinally adjacent first portions 120. In some embodiments, for example as shown in FIG. 1D, the first portions 120a of the first spines 106a are longitudinally staggered relative to the first portions 120b of the second spines 106b such that the first portions 120a of the first spines 106a and the first portions 120b of the second spines 106b are coextensive along only a portion of their respective lengths.

As best shown in FIG. 1D, the expandable device 101 may comprise a plurality of spine regions 121, each comprising a circumferential band of circumferentially adjacent first portions 120 and the four struts 110 coupled to each of the first portions 120. Each of the spine regions 121 may be longitudinally disposed between second end portions 122 on either side of the respective first portions 120. In those embodiments where the expandable device 101 comprises first and second spines 106a, 106b, the expandable device 101 may comprise first spine regions 121a along the first spines 106a and second spine regions 106b along the second spines 106b. The first portions 120 within the first spine regions 121a may be generally circumferentially aligned and the first portions 120 within the second spine regions 121b may be generally circumferentially aligned, while the first portions 120 in the first spines regions 121a and the first portions 120 in the second spine regions 121b may be circumferentially offset.

The expandable device 101 may comprise different numbers of first and second spine regions 121a, 121b. For example, in the embodiments represented by FIG. 1D, the expandable device 101 comprises three first spine regions 121a and two second spine regions 121b. In other embodiments, the expandable device 101 may comprise more or fewer first spine regions 121a and/or more or fewer second spine regions 121b. In the embodiments represented by FIG. 1D, each of the spine regions 121 comprise 12 first portions 120 and 48 struts 110, and the expandable device 101 is approximately 25 mm long with 60 total first portions 120 and 144 total struts 110. In other embodiments, the expandable device 101 may be longer or shorter and/or comprise more or fewer than 12 first portions 120 per spine region 121 (e.g., 1, 2, 3, 4, 5, 6, 7, 8, 9, 10, 11, 13, 14, 15, 16, 17, 18, 19, 20, 22, 23, 24, etc. first portions 120 per spine region 121), one or more buckled portions 150 within a given spine region 121 and/or first portion 120, more or fewer than 48 struts 110 per spine region 121 (e.g., 0, 2, 4, 6, 8, 10, 12, 14, 16, 18, 20, 22, 24, 26, 28, 30, 32, 36, 40, 44, 52, 56, 60, 64, 68, 72, 76, 80, etc. struts 110 per spine region 121), more or fewer than 60 total first portions 120, and/or more or fewer than 144 total struts 110. The first and second spine regions 121 may have the same or different numbers of first portions 120 and/or struts 110. Within one, some, non, or all of the spine regions 121, the strut 110 to first portion 120 ratio may be 2 to 1, 3 to 1, 4 to 1, 5 to 1, 6 to 1, 7 to 1, 8 to 1, and others.

The first and second spine regions 121a, 121b may overlap along the longitudinal axis of the expandable device 101 (as shown in FIG. 1D), or the first and second spine regions 121a, 121b may be longitudinally adjacent one another, or spaced apart. In some embodiments, the expandable device 101 includes some overlapping spine regions 121 and some adjacent or spaced apart spine regions 121. The spine regions 121 may overlap, for example, by the length of a strut region 102 such that longitudinally overlapping spine regions 121 share a strut region 102.

Figure 2A:
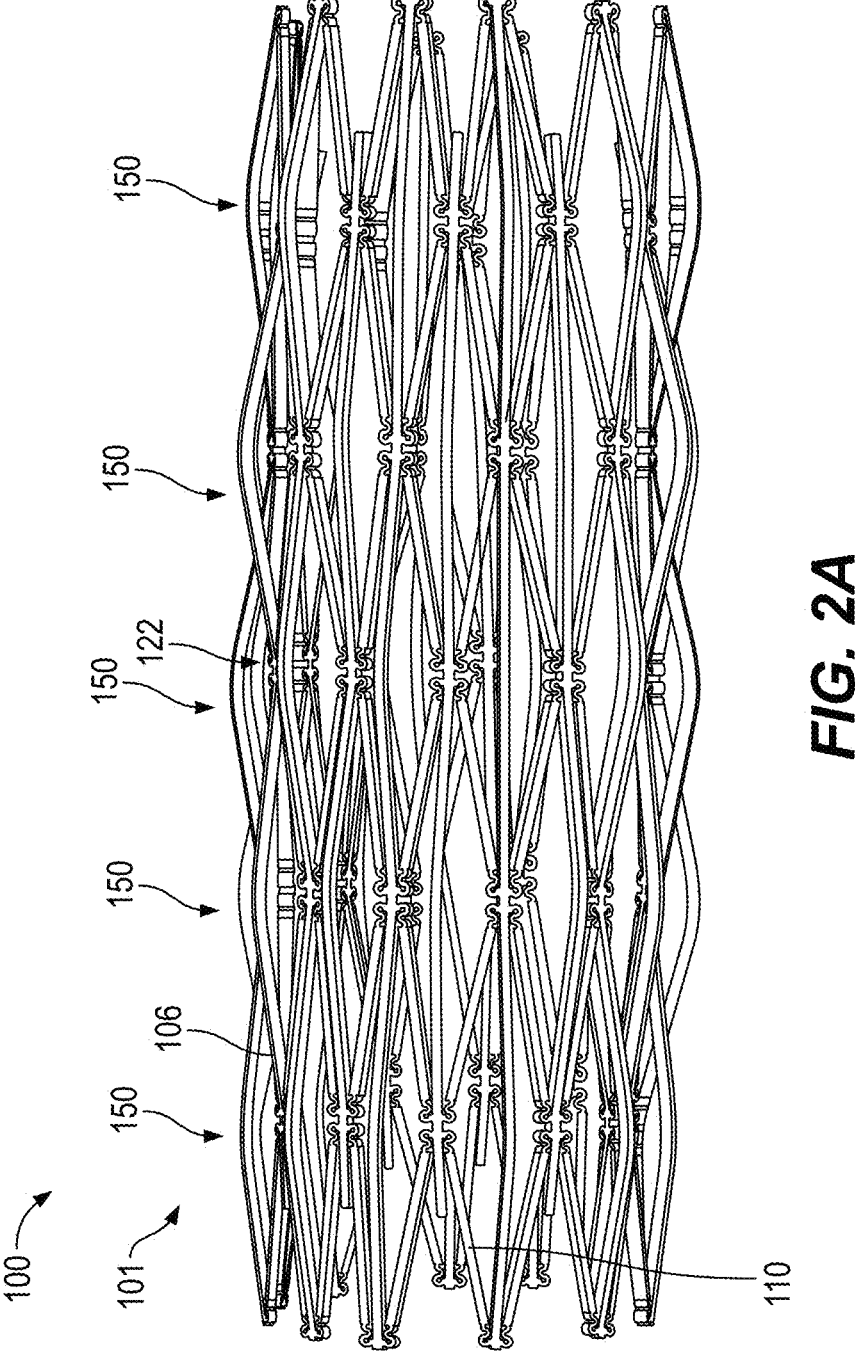
FIG. 2A is a side view of the expandable device shown in FIGS. 1A-1D in an intermediate expanded configuration in accordance with embodiments of the present technology.
Figure 2B:
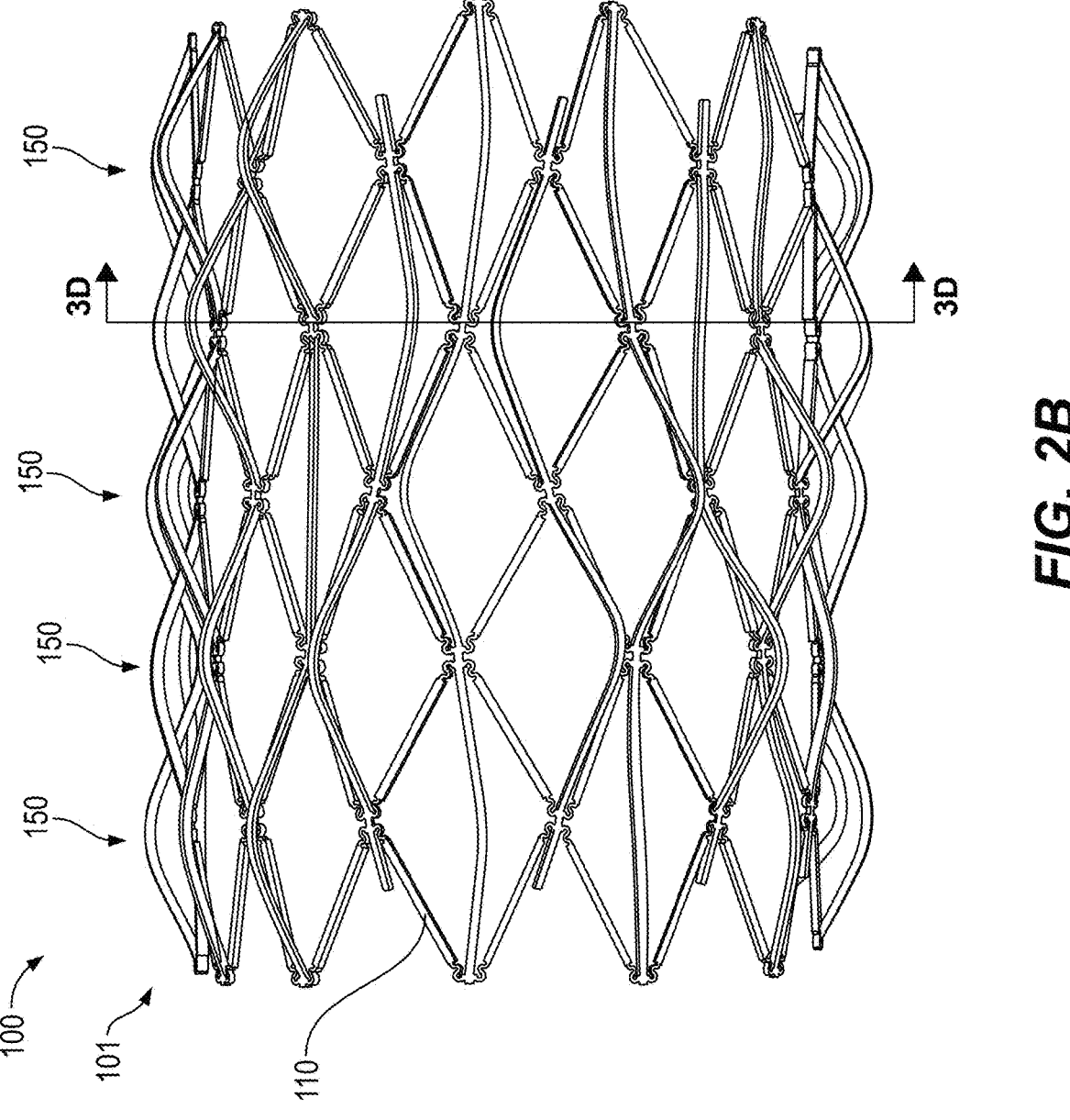
FIG. 2B is a side view of the expandable device shown in FIGS. 1A-1D in a fully expanded configuration in accordance with embodiments of the present technology.
Figure 2C:
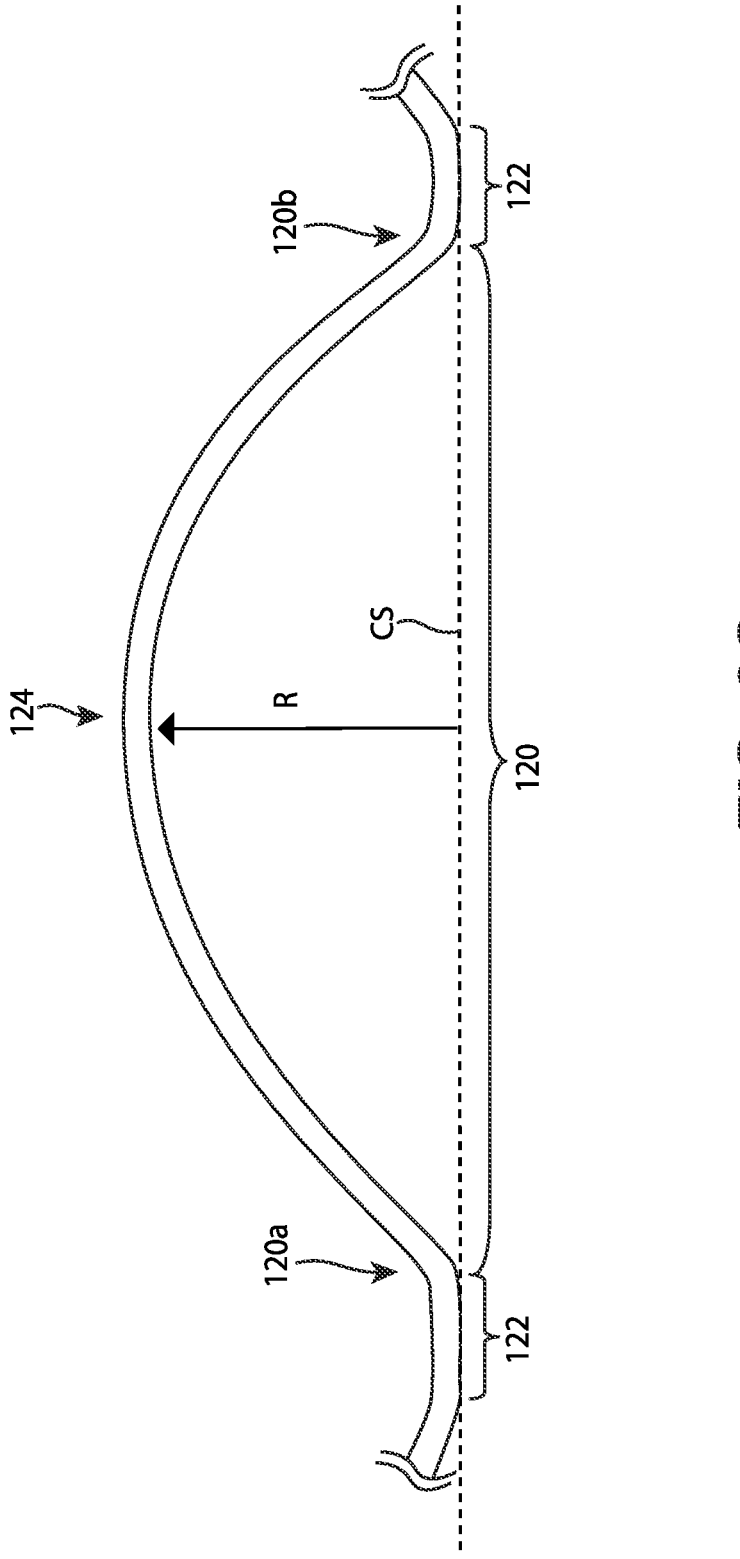
FIG. 2C is a side view of a portion of a spine configured in accordance with the present technology, shown isolated from an expandable device in an expanded configuration.

FIGS. 2A and 2B are side views of the expandable device 101 in an intermediate expanded configuration and a fully expanded configuration, respectively, and FIG. 2C is a side view of one of the first portions 120 of the spines 106 when the expandable device 101 is in the fully expanded configuration. According to some embodiments, for example as depicted in FIGS. 2A-2C, transformation of the expandable device 101 from the collapsed configuration to the expanded configuration causes the first portions 120 to bow out of a substantially cylindrical surface CS defined by the second portions 122 such that, at least in the expanded configuration, the first portions 120 form a plurality of buckled portions 150 extending radially away from the rest of the sidewall. The buckled portions 150, for example, may be disposed along one or more of the spines 106 and may be spaced apart about a length and/or circumference of the expandable device 101.

In some embodiments, for example as shown in FIGS. 2A-2C, the buckled portions 150 comprise arched regions of the respective spine 106. The buckled portions 150 can have a peak region 124 between the first and second end portions 120a, 120b, where the peak region 124 comprises a location or region of the buckled portion 150 that is radially farthest from the second portions 122. As discussed herein, a radial distance R measured between (a) the cylindrical surface CS defined by the plurality of second portions 122 and (b) the peak regions 124 of the buckled portions 150 defines a thickness of the annular lumen created by the buckled portions 150.

Each of the buckled portions 150 may span two strut regions 102, as shown. In some embodiments, one, some, or all of the buckled portions 150 span more than two strut regions 102 (e.g., three strut regions, four strut regions, etc.).

The first spines 106a may have fewer buckled portions 150 than the second spines 106b, or vice versa. In some embodiments, the first and second spines 106a, 106b have the same number of buckled portions 150. One, some, none, or all of the spines 106 may have a single buckled portion 150. The length of the buckled portions 150 along a given spine 106 may be the same or may vary, and the length of the second portions 122 along a given spine 106 may be the same or vary. Additionally or alternatively, the buckled portions 150 of some or all of the spines 106 may have different lengths.

Figures 3A, 3B:
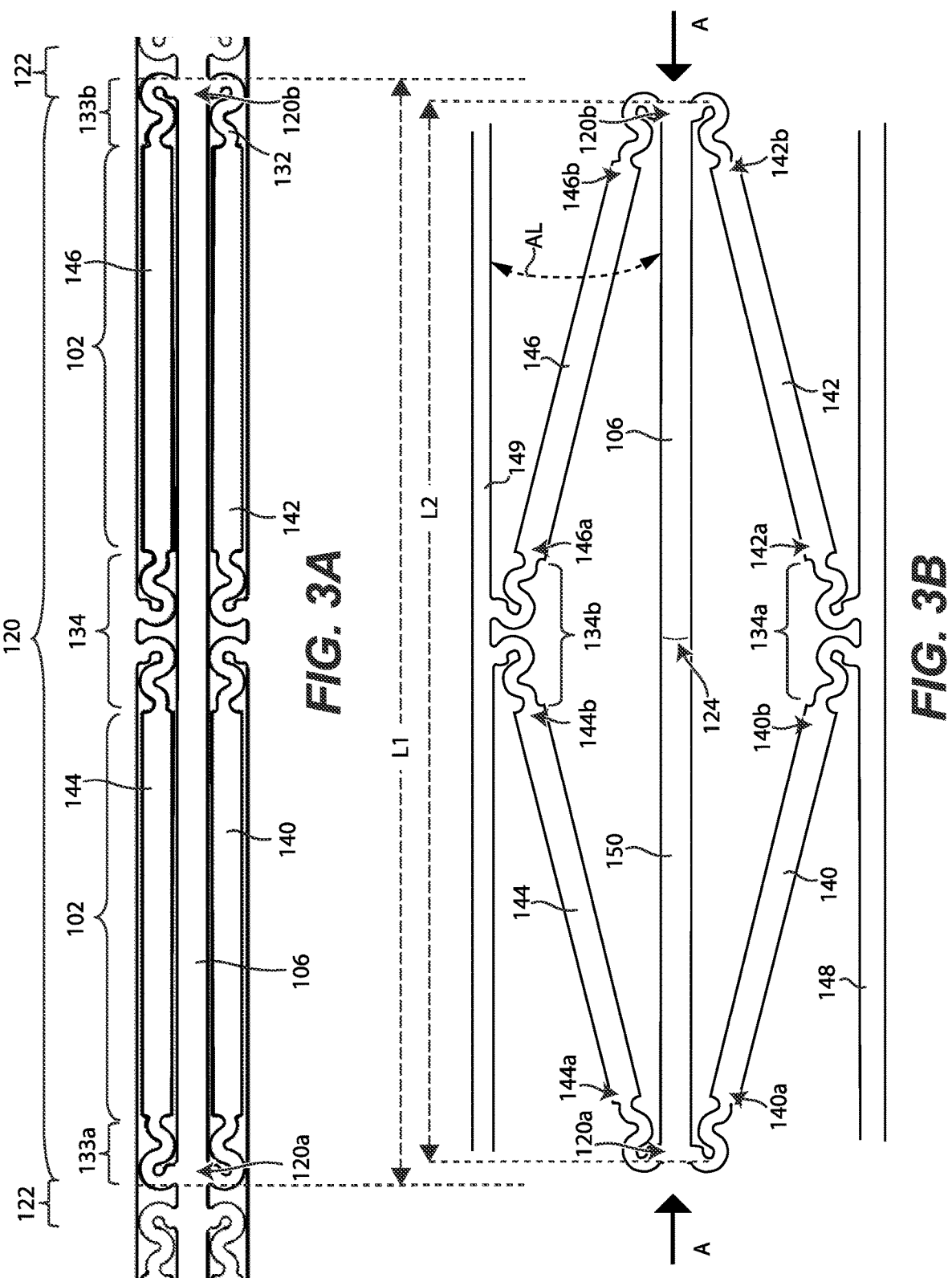
FIG. 3A is an enlarged portion of an expandable device configured in accordance with several embodiments of the present technology, shown in a collapsed configuration.
FIG. 3B is an enlarged portion of an expandable device configured in accordance with several embodiments of the present technology, shown in an expanded configuration.
Figure 3C:
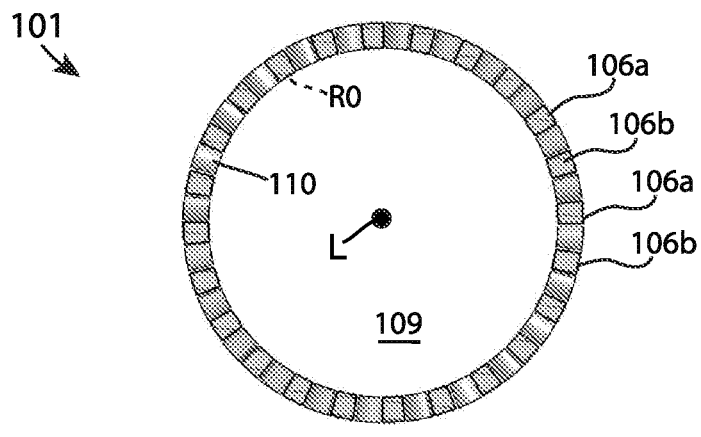
FIG. 3C is an axial cross-sectional view of the expandable device in a collapsed configuration, as shown in FIG. 1A, taken along line 3C-3C.
Figure 3D:
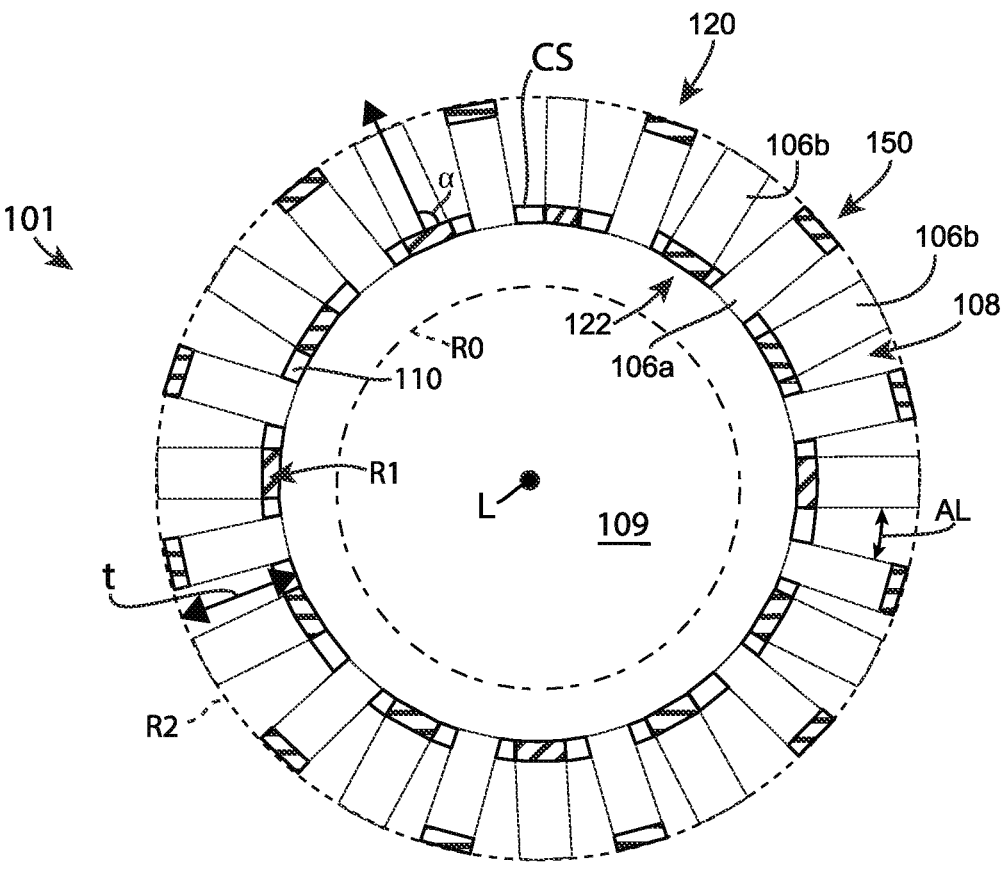
FIG. 3D is an axial cross-sectional view of the expandable device in an expanded configuration, as shown in FIG. 2B, taken along line 3D-3D.

According to some embodiments, movement of the struts 110 during radial expansion of the expandable device 101 may axially compress portions of the spines 106, thereby causing the first portions 120 to bow away from the cylindrical surface CS and form the buckled portions 150. For example, FIGS. 3A and 3C depict a portion of the expandable device 101 in a collapsed configuration, and FIGS. 3B and 3D show a portion of the expandable device 101 in an expanded configuration. The portion shown in FIGS. 3A and 3C includes a first portion 120 of one of the spines 106 and second portions 122 at either longitudinal end of the first portion 120, as well as first, second, third and fourth struts 140, 142, 144, and 146 coupled to the first portion 120 of the spine 106 via joints 132 at the first and second pairs of joints 133a, 133b. At least in the collapsed configuration, the first and second end portions 120a, 120b of the first portion 120 may be separated along the longitudinal axis of the expandable device 101 by a first length L1, and circumferentially adjacent spines 148, 149 may be separated from the spine 106 by an arc length AL. Also in the collapsed configuration, as best shown in FIG. 3C, the struts 110 (including struts 140, 142, 144, 146) and the spines 106 may be substantially the same radial distance, R0, from a central longitudinal axis L of the expandable device 101 and together define a main lumen 109.

In the enlarged portion of the expandable device 101 shown in FIGS. 3A and 3B, a first end portion 140a of the first strut 140 is connected to a first end portion 120a of the first portion 120 of the spine 106, and a second end portion 140b of the first strut 140 is connected to a second portion 122 of a first circumferentially adjacent spine 148 (only a portion shown) or other structural member of the sidewall. A first end portion 142a of the second strut 142 is connected to the second portion 122 of the first circumferentially adjacent spine 148 (only a portion shown) or other structural member of the sidewall, and a second end portion 142b of the second strut 142 is connected to a second end portion 120b of the first portion 120 of the spine 106. A first end portion 144a of the third strut 144 is connected to the first end portion 120a of the first portion 120 of the spine 106, and a second end portion 144b of the third strut 144 is connected to a second portion 122 of a second circumferentially adjacent spine 149 (only a portion shown) or other structural member of the sidewall. A first end portion 146a of the fourth strut 146 is connected to the second portion 122 of the second circumferentially adjacent spine 149 (only a portion shown) or other structural member of the sidewall, and a second end portion 146b of the fourth strut 146 is connected to the second end portion 120b of the first portion 120 of the spine 106.

Radial expansion of the expandable device 101 increases the radial distance between (a) the spines 106 and (b) the longitudinal axis L of the expandable device 101, which in turn increases an arc length AL between circumferentially adjacent spines 106. As the circumferential distance between the spines 106 increases, the struts 110 angle away from the spines 106 to which they are attached. For example, as shown in FIG. 3B, as the arc lengths AL between the spine 106 and the circumferentially adjacent spines 148, 149 increase, (a) the second end portion 140b of the first strut 140 and the first end portion 142a of the second strut 142 together move away from the spine 106 in a first circumferential direction (e.g., with node 134a), and (b) the second end portion 144b of the third strut 144 and the first end portion 146a of the fourth strut 146 move away from the spine 106 in a second circumferential direction (e.g., with node 134b) opposite the first circumferential direction. As a result, the end portions 140a and 142b, and 144a and 146b of the struts 140, 142, 144, 146 attached to the spine 106 are pulled longitudinally toward one another, and in so doing force the attached end portions 120a, 120b of the first portion 120 of the spine 106 along with them (indicated by arrows A in FIG. 3B). This movement longitudinally compresses the spine 106 so that a longitudinal distance between the first and second end portions 120a, 120b of the spine 106 decreases from the first length L1 in the collapsed configuration to a shorter second length L2. To accommodate this axial compression, the first portions 120 bow outwardly from the second portions 122 to form buckled portions 150. Accordingly, as best shown in FIG. 3D, when the expandable device 101 is in the expanded configuration, (a) the struts 110 and the second portions 122 of the spines 106 are a first radial distance R1 from the central longitudinal axis L, and (b) the first portions 120 of the spines 106 are a second, greater radial distance R2 from the central longitudinal axis L.

According to some embodiments, for example as shown in FIG. 3D, when the expandable device 101 is in the expanded configuration, the expandable device 101 defines two lumens. The expandable device 101 may have a first, main lumen 109 defined by the radially aligned struts 110 and the second portions 122 of the spines 106, and a second, annular lumen 108 between (a) the peak regions 124 of first portions 120 of the spines 106 and (b) the struts 110 and the second portions 122 of the spines 106. The annular lumen 108 may have a thickness t measured between (a) the peak regions 124 of first portions 120 of the spines 106 and (b) the struts 110 and the second portions 122 of the spines 106. The dual lumens of the expandable devices 101 of the present technology can be especially beneficial for reinforcing or creating an opening through a conduit while maintaining flow through or into the conduit. The annular lumen 108 created by the buckled portions 150 provides a flow passage through the conduit while the actuator is expanded in the main lumen 109. Additional details and specific applications of this feature of the present technology are discussed elsewhere herein.

Figure 4A:
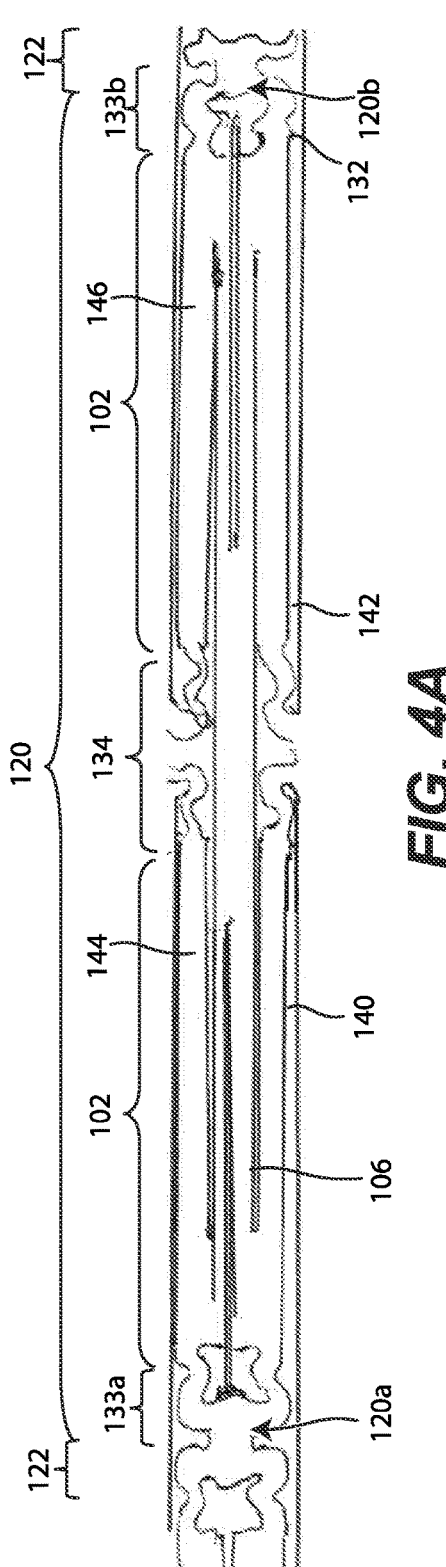
FIG. 4A is an enlarged portion of an expandable device configured in accordance with several embodiments of the present technology, shown in a collapsed configuration.
Figure 4B:
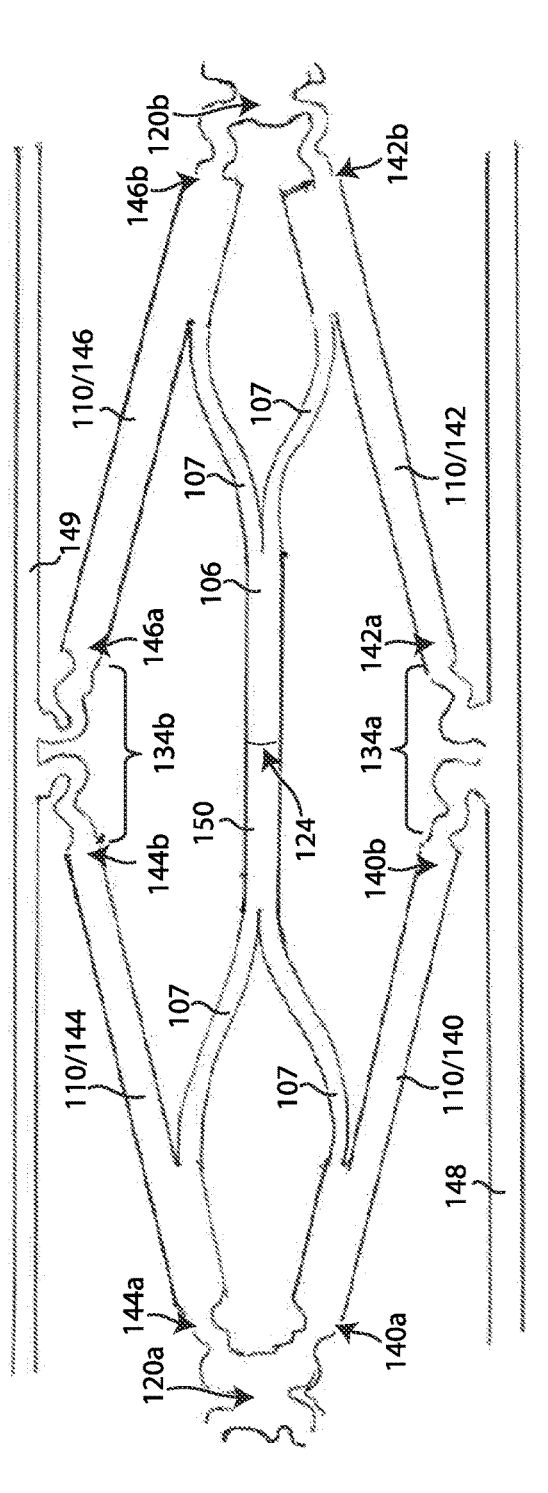
FIG. 4B is an enlarged portion of an expandable device configured in accordance with several embodiments of the present technology, shown in an expanded configuration.

According to some embodiments, for example as shown in FIG. 3D, the buckled portions 150 may extend radially away (outwardly or inwardly) from the substantially cylindrical surface CS at an angle α that is approximately 90 degrees. In some embodiments, one, some, or all of the buckled portions 150 may extend radially away from the substantially cylindrical surface CS as an angle other than 90 degrees (not shown). In some cases, however, it may be beneficial to ensure that one, some, or all of the buckled portions 150 extend radially away (outwardly or inwardly) from the substantially cylindrical surface CS at approximately 90 degrees. In such embodiments, it may be beneficial to configure the spines 106 and/or struts 110 to improve the directional stability and/or angular predictability of the buckled portions 150. For example, as shown in FIGS. 4A and 4B, in some embodiments one, some, or all of the first portions 120 of the spines 106 have end portions that connect directly to the struts 110 rather than to the second portions 122 or end pairs 133. The first portions 120 may branch into two legs 107 at each of its ends, and each of the legs 107 may connect to one of the struts 110. As a result, as the struts 110 expand circumferentially and the spines 106 start to buckle, the legs 107 establish a broader lateral support for the spines 106 and guide the buckled portions 150 into an orientation relative to the rest of the expandable device 101 that is about 90 degrees. Additionally or alternatively, the first portions 120 of the expandable device 101 may be pre-formed (e.g., via heat treatment) to encourage the creation of buckled portions 150 of a desired orientation.

Figures 5A, 5B:
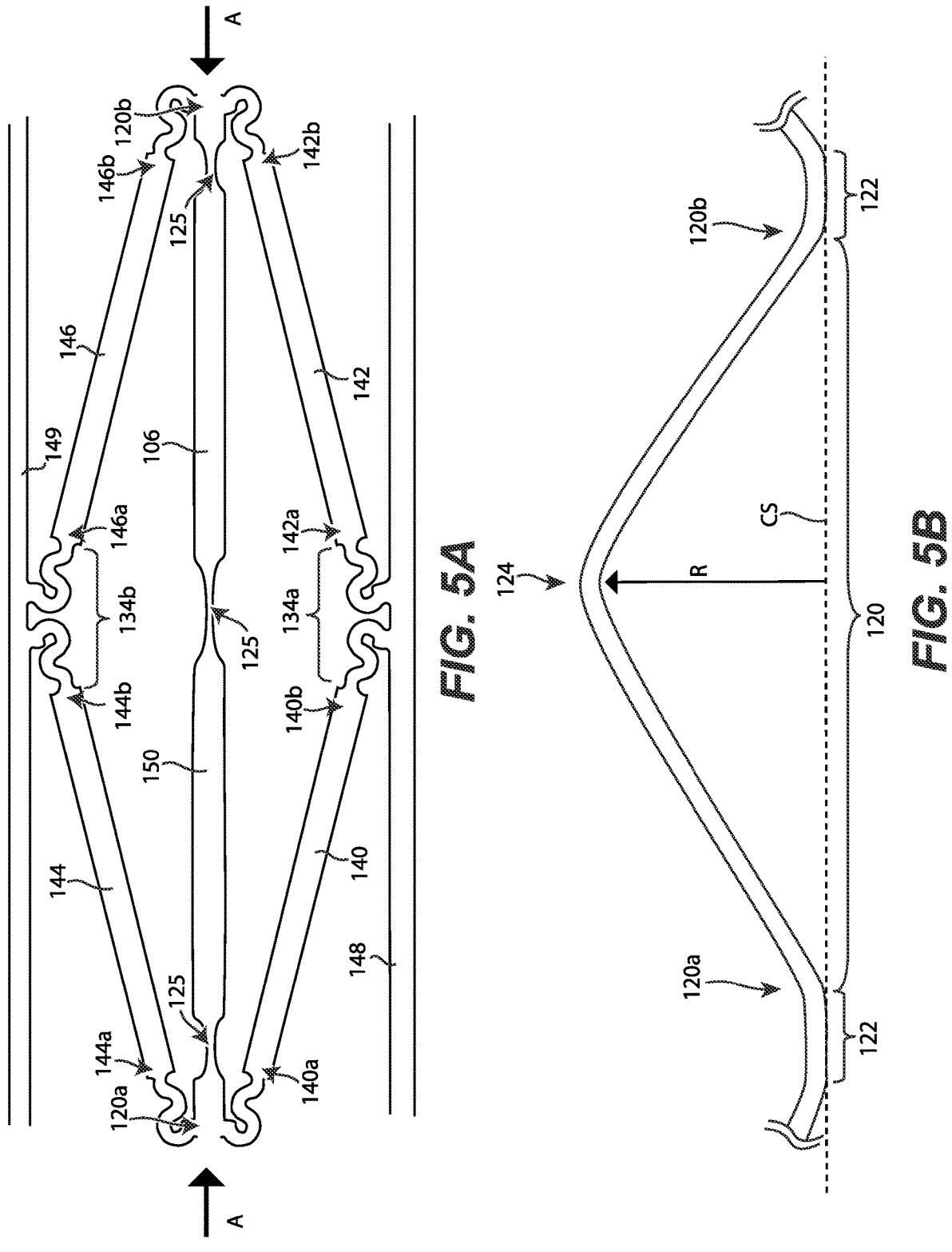
FIG. 5A is an enlarged portion of an expandable device configured in accordance with several embodiments of the present technology, shown in an expanded configuration.
FIG. 5B is a side view of a portion of a spine configured in accordance with the present technology, shown isolated from the portion of the expandable device in FIG. 5A.

In some embodiments, the thickness and/or width of the spines 106 (along the first portions 120 and/or second portions 122) may be varied to achieve a desired buckling profile, and/or all or portions of the spines 106 may be pre-formed with bends at particular locations and/or with particular shapes. One, some, or all of the first portions 120 may have a substantially constant thickness and/or width along their lengths (for example as shown in FIGS. 3A and 3B), which produces a single peak 124 and a more sinusoidal buckling profile. As shown in FIGS. 5A and 5B, in some embodiments one, some, or all of the first portions 120 may have a relief 125 at the desired peak location, and optionally near the first and second end portions 120a, 120b. The relief 125 may be formed by a length of the spine 106 having a reduced width (as shown), and/or may comprise a length of the spine 106 having a reduced thickness. Because of the reliefs 125, the resulting buckled portion 150 has tighter bends and takes on a more triangular shape, as shown in FIG. 5B. This peak may be relatively centered along the length of the spine, as shown in FIG. 5B, or it may be closer to one end of the spine, to give an asymmetric buckling profile. Additionally or alternatively, the reliefs 125 may be configured so that the buckled portions 150 have relatively flat peaks 124 (as compared to the "pointier" peaks 124 shown in FIG. 5B), thereby providing more surface area for engaging the apposing material, expandable device, actuator, or other device. The flatter peaks may also provide less traumatic surfaces for engaging different apposing materials.

Figures 6A, 6B:
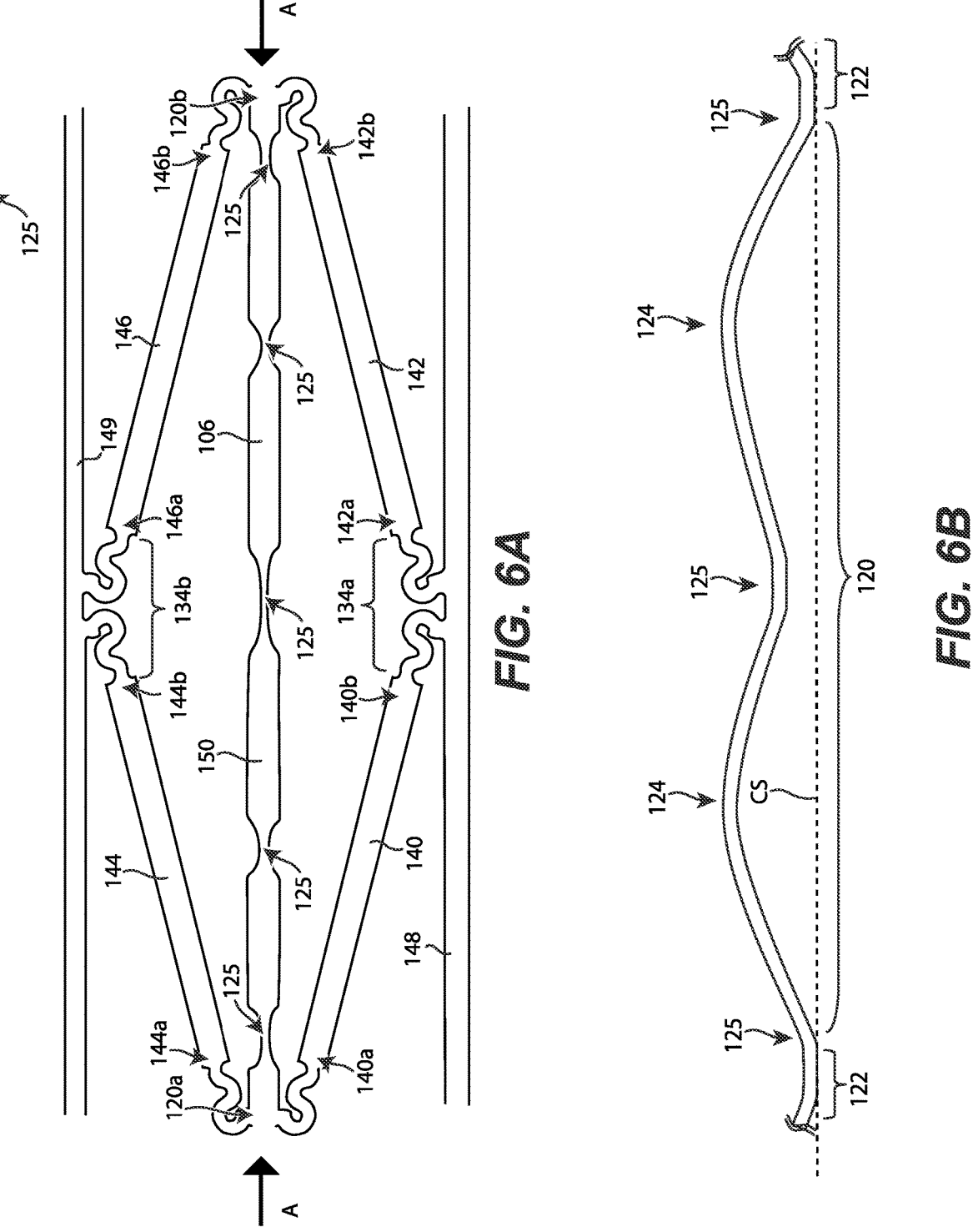
FIG. 6A is an enlarged portion of an expandable device configured in accordance with several embodiments of the present technology, shown in an expanded configuration.
FIG. 6B is a side view of a portion of a spine configured in accordance with the present technology, shown isolated from the portion of the expandable device in FIG. 6A.

In some embodiments, for example as shown in FIGS. 6A and 6B, one, some, or all of the first portions 120 may have multiple reliefs 125 such that the first portion 120 forms two or more buckled portions 150 (or two or more peaks 124) when the expandable device 101 is radially expanded. In such embodiments, the valley between the buckled portions 150 may be radially farther from central longitudinal axis than the second portions 122 and/or struts 110. The first portions 120 along a particular spine 106: (a) may form the same or different numbers of buckled portions 150 per first portion 120, (b) may form buckled portions 150 having the same or different shapes or profiles, and/or (c) may be the same or different lengths. The first portions 120 within a particular spine region 121: (a) may form the same or different numbers of buckled portions 150 per first portion 120, (b) may form buckled portions 150 having the same or different shapes or profiles, and/or (c) may be the same or different lengths.

Figure 7:
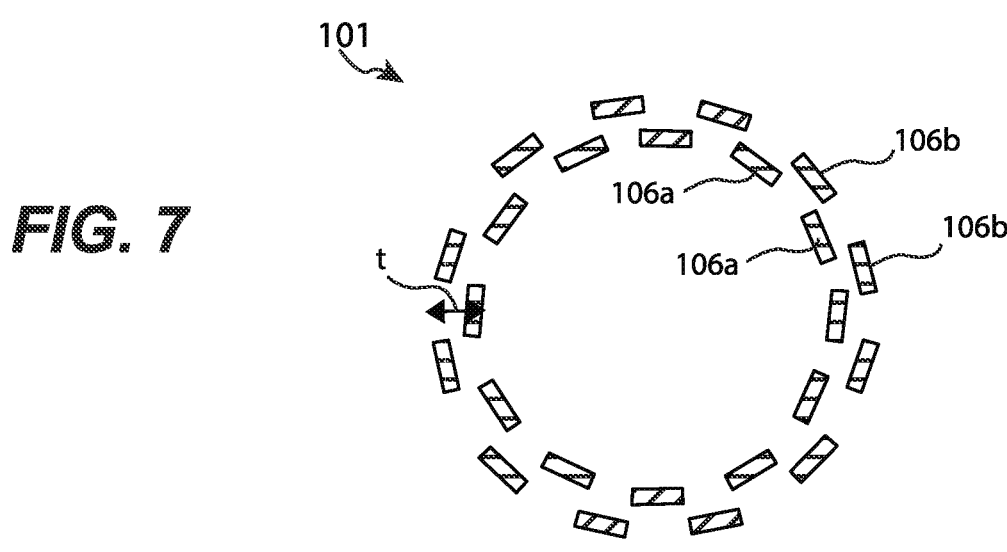
FIGS. 7 and 8 are axial cross-sectional views of expandable devices configured in accordance with embodiments of the present technology.
Figure 8:
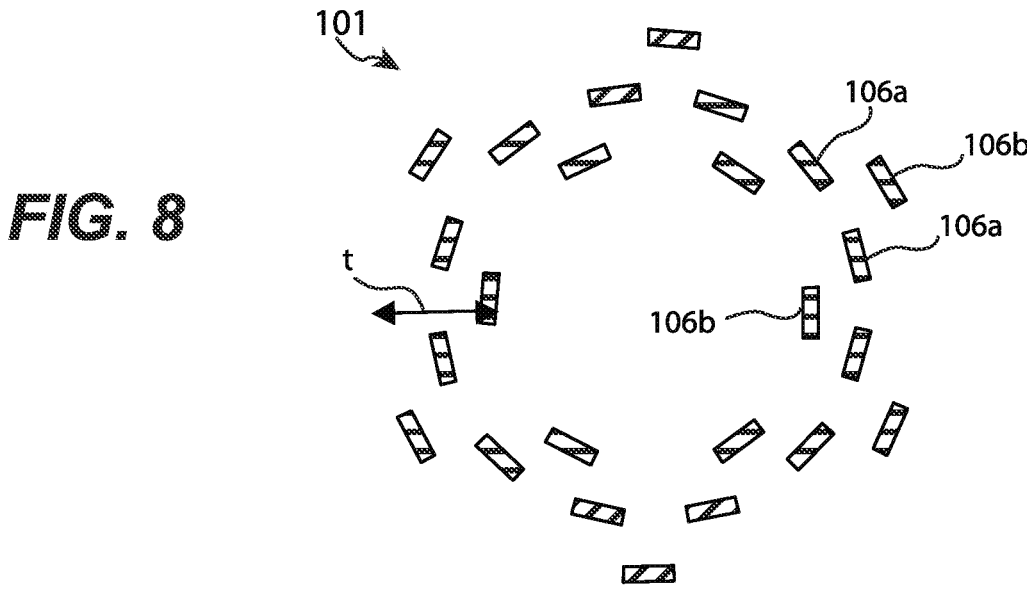

In some cases, as the expandable device 101 is expanded radially, the spines 106 might be inclined to buckle in different directions, with some buckling radially outward and some buckling radially inward. In some instances it may be preferable to encourage all of the buckled portions 150 to extend in the same direction. To encourage this, the expandable device 101 may be pre-formed (for example, via heat treatment) so that all of the first portions 120 of the spines 106 buckle in the same desired radial direction (i.e., radially inward or outward). For example, some or all of the expandable device 101 may be pre-formed to a relaxed, unconstrained diameter which is approximately the diameter of the overall delivery catheter, so that even after the expandable device has been delivered and the expandable device 101 is at its relaxed size, the relaxed device can be removed through the sheath or guiding catheter. Additionally or alternatively, as depicted in FIG. 7, in some applications it may be preferable to have all of the buckled portions 150 buckle radially inwardly. As shown in FIG. 8, in some embodiments the spines 106 may buckle radially inwardly and radially outwardly, thereby producing twice the thickness t as compared to an expandable device where all of the buckled portions 150 extend in the same radial direction.

According to some embodiments, the expandable device 101 of the present technology is self-expanding. For example, all or a portion of the expandable device 101 may comprise a material with superelastic properties, such as Nitinol. In some or all of such embodiments, the expandable device may form a small-diameter tube in its relaxed state. The expandable device 101 may also be heat treated and/or pre-shaped so that in its relaxed, unconstrained state it has a diameter that is less than the fully expanded diameter of the device. In such embodiments, the expandable device 101 may collapse down its smaller relaxed diameter. Additionally or alternatively, the expandable devices 101 of the present technology may comprise a plastically deforming sidewall, such as a sidewall manufactured from a polymer, stainless steel, or cobalt-chromium alloy.

III. Other Design Details

In some embodiments, the expandable device may comprise at least two nested expandable devices, each having buckled portions. The expandable devices may be arranged so that their buckled portions face towards and/or away from one another. Depending on how the outer expandable device is positioned relative to the inner buckling expandable device, the outer expandable device may further increase the annular thickness of the expandable device. However, it may be advantageous to configure the outer expandable device with the buckling elements predisposed to buckle radially inwards, and to align these buckles such that they follow the buckling elements of the inner expandable device 101. In this way, both the inner and outer surfaces will have flat diamond-shaped patterns, which will press against material apposing the inner surface of the expandable device and the outer surface of the expandable device, respectively.

As the expandable device expands, there will be significant stresses within the expandable device. The swinging struts will be under tension as they expand and create the force which compresses and longitudinally foreshortens the buckling spines. The expandable device strut widths and hinge details are configured to accommodate these stresses.

Along an intermediate portion of the expandable device, since there are additional struts all around each cell of the expandable device, the expandable device should hold its cylindrical shape. However, at the ends of the expandable device, there may be nothing holding the free termini of the spines in the cylindrical surface of the expandable device 101 when the expandable device is radially expanded. These free termini may be inclined to bend radially inwards or outwards. In some embodiments, these bending free termini can be employed as additional securing members. However, in some embodiments such radial bending of the spines (or struts) at the end portions of the expandable device may not be preferable. To control these ends, any of the expandable devices described herein may include one or more extension members (not shown) extending beyond the end termini of one, some, or all of the spines 106 to help hold the spines 106 and other structural members of the expandable device 101 in the cylindrical surface of the non-buckled portions of the expandable device 101. The extension members might be connected at their other ends to solid rings which fit around the delivery catheter. These rings may slide longitudinally as the expandable device expands.

Additionally or alternatively, the expandable device may comprise a plurality of eyelets and/or loops (not shown) at the ends of the spines 106 and a connector threaded through the eyelets to control the ends of the expandable device. In some embodiments, the eyelets or loops may additionally or alternatively be placed at other longitudinal locations along the expandable device. The connector may be, for example, a fiber or suture that is threaded in a zig-zag pattern through the eyelets. As the expandable device expands, the spines may compress longitudinally and the zig-zag pattern may become circular. When the expandable device is fully expanded, the connector may be taut, limiting the expansion of the expandable device ends and keeping them from buckling outwards from the cylindrical surface of the expandable device.

Additionally or alternatively, the expandable device may comprise a valve attached to the expandable device. This could be a valve which expands within the central lumen of the expandable device, or a valve which covers at least one end of the annular lumen defined by the expandable device in its expanded shape. The valve could be a duckbill, windsock, tricuspid, or other valve. It could be designed to open and close over an element placed through the central lumen of the expanded device, or it could be designed to open and close in the absence of anything placed inside the expandable device.

Additionally or alternatively, the expandable device may comprise a tubular sleeve disposed within the expandable device. This tubular material could form a luminal separation between the central lumen and annular lumen formed by the expandable device in its expanded state. The tubular material could be attached to one or a plurality of struts and/or spines of the expandable device.

Additionally or alternatively, the expandable device may comprise a tubular sleeve disposed around the outside of the expandable device. The tubular material could be attached to one or a plurality of struts and/or spines of the expandable device.

IV. Selected Examples of Manufacturing

In some embodiments, the expandable device may be formed by laser-cutting the desired pattern into a tubular sheet of material. In certain embodiments, the expandable device may be initially formed as a flat sheet of material having a pattern of struts and spines. The struts and spines may be formed by depositing a thin film on a flat surface in the desired pattern, or by laser-cutting a desired pattern into the flat sheet of material. The flat pattern may then be curled up into a generally tube-like shape such that the longitudinal edges of the flat pattern are positioned adjacent to or in contact with one another. The longitudinal edges can be joined (e.g., via laser welding) along all or a portion of their respective lengths. In some embodiments, the struts and spines may be formed by depositing a thin film on the surface of a tubular frame in a desired pattern (e.g., via thin film deposition, vapor deposition, or combinations thereof).

According to several embodiments, all or a portion of the expandable device may be heat treated in its desired fully expanded configuration, or in a configuration having a diameter smaller than is intended when the expandable device is implanted. Heat treating the mesh may be beneficial for preferential bending at certain locations and may reduce or substantially remove any stresses that accompany forcing the mesh from its collapsed or unexpanded configuration into the expanded configuration. To help achieve a desired shape in the expanded configuration, one or more portions of the mesh may be thinned to form a preferential bending location.

In some embodiments, the expandable device 101 could be formed at an intermediate diameter between its constrained state and fully expanded state as a way to reduce the amount of strain that hinge connecters are exposed to in a given direction (if the hinge connector opens by 60 degrees from tubular to expanded state, then heat shaping at 30 degrees open allows the hinge connector to only experience 30 degrees of deflection from its heat-shaped state; this could potentially reduce the likelihood of fracture at hinges). In some embodiments, the self-expanding expandable device 101 could be heat treated and/or pre-shaped so that in its relaxed, unconstrained state it is fully expanded.

As described herein, in some cases it may be beneficial to pre-expand the expandable device just enough to ensure that the struts buckle in the desired direction. This pre-expansion processing could be as simple as expanding the expandable device on a very gently tapered mandrel, making sure that all of the struts are buckled in the right direction (radially inward or outward), and then annealing the expandable device in this shape. If it is desired to have the struts buckle radially inward, the tapered forming mandrel might have longitudinal slots into which the struts can buckle. The ends of the expandable device also could be folded over longitudinally to form softer rounded ends if that is desired.

After any pre-forming and annealing, the expandable device may optionally be electropolished to minimize any sharp edges.

CONCLUSION

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

We claim:

1. An expandable device comprising:

a collapsed configuration and an expanded configuration in which the expandable device is configured to be positioned in a conduit, a plurality of spines and a plurality of struts, the spines extending along a longitudinal axis of the expandable device and the struts connecting adjacent spines, wherein:

the spines include a spine having first and second end portions, each of the first and second end portions branching into a first leg and a second leg, the struts include a first strut, a second strut, a third strut, and a fourth strut, the first, second, third, and fourth struts being linear, wherein— the first strut having first and second end portions, wherein the first end portion of the first strut is connected to the first end portion of the third strut, the second strut having first and second end portions, wherein the second end portion of the second strut is connected to the second end portion of the fourth strut, the first leg of the first end portion of the spine is connected to the first strut between the first and second end portions of the first strut, the second leg of the first end portion of the spine is connected to the third strut between the first and second end portions of the third strut, the first leg of the second end portion of the spine is connected to the second strut between the first and second end portions of the second strut, the second leg of the second end portion of the spine is connected to the fourth strut between the first and second end portions of the fourth strut, wherein radial expansion of the expandable device decreases a longitudinal distance between the first end portion of the first strut and the second end portion of the second strut, decreases a longitudinal distance between the first end portion of the third strut and the second end portion of the fourth strut, and decreases a longitudinal distance between the first and second end portions of the spine, thereby causing the spine to buckle out of radial alignment with the first, second, third, and fourth struts.

2. The expandable device of claim 1, wherein the first, second, third, and fourth struts are substantially linear in the collapsed configuration and in the expanded configuration.

3. The expandable device of claim 2, wherein each first end portion and each second end portion of the first, second, third, and fourth struts comprises a flexible joint.

4. The expandable device of claim 1, wherein, when the expandable device is in the collapsed configuration, the first, second, third, and fourth struts are substantially parallel to the spine.

5. The expandable device of claim 1, wherein the second end portion of the first strut and the first end portion of the second strut are fixed relative to one another at a node.

6. The expandable device of claim 5, wherein the spine is a first spine and the expandable device further comprises a second spine having first and second end portions, each of the first and second end portions branching into a first leg and a second leg, a fifth strut having first and second end portions, and a sixth strut having first and second end portions, and wherein— the second end portion of the fifth strut is coupled to the node, the first end portion of the sixth strut is coupled to the node, the second leg of the first end portion of the second spine is connected to the fifth strut at a linear portion of the fifth strut between the first and second end portions of the fifth strut, the second leg of the second end portion of the second spine is connected to the sixth strut at a linear portion of the fifth strut between the first and second end portions of the sixth strut, and radial expansion of the expandable device decreases a longitudinal distance between the first end portion of the fifth strut and the second end portion of the sixth strut, and decreases a longitudinal distance between the first and second end portions of the second spine, thereby causing the second spine to buckle out of radial alignment with the fifth and sixth struts.

7. The expandable device of claim 6, wherein, when the expandable device is in the collapsed configuration, the first, second, third, fourth, fifth, and sixth struts are substantially parallel to the first and second spines.

8. The expandable device of claim 6, wherein, when the expandable device is in the expanded configuration, the first, second, fifth and sixth struts angle away from the first and second spines, thereby forming an X where the node is at the intersection of the X.

9. The expandable device of claim 6, wherein, when the expandable device is in an expanded configuration, the node, the first strut, the second strut, the fifth strut, and the sixth strut are substantially radially aligned at a first radial location and the first and second spines are radially offset from the first radial location and disposed at a second radial location.

10. The expandable device of claim 6, wherein the second end portion of the fifth strut and the first end portion of the sixth strut are fixed relative to one another at the node.

11. The expandable device of claim 1, wherein the expandable device is configured to be expanded via expansion of an actuator positioned within a central lumen of the expandable device.

12. The expandable device of claim 1, further comprising a valve coupled to the expandable device.

13. The expandable device of claim 1, wherein the expandable device comprises a superelastic material.

14. The expandable device of claim 1, wherein the connections between at least some of the struts and spines are hinges.

15. The expandable device of claim 1, wherein the conduit is a pipe.

16. The expandable device of claim 1, wherein the expandable device is configured to be expanded within another expandable device.

17. The expandable device of claim 1, further comprising a tubular membrane bonded to at least some of the struts defining an inner lumen of the expandable device, at least some of the spines defining the inner lumen of the expandable device, or at least some of the struts and at least some of the spines defining the inner lumen of the expandable device.

18. The expandable device of claim 1, further comprising a tubular membrane bonded to at least some portions of some of the spines defining an outer lumen of the expandable device.

19. The expandable device of claim 1, wherein the expandable device has been heat set at an intermediate expanded configuration, the intermediate expanded configuration having a diameter between a diameter of the expandable device in the collapsed configuration and a diameter of the expandable device in a fully expanded configuration.

20. The expandable device of claim 1, wherein the expandable device has been heat set at a fully expanded configuration.

21. The expandable device of claim 1, wherein the expandable device comprises a material that has been heat set.

22. The expandable device of claim 1, wherein the conduit is configured to receive petroleum therethrough.

23. The expandable device of claim 1, wherein the conduit is a tubular support structure.

24. The expandable device of claim 1, wherein the conduit is an opening in a wall.

25. The expandable device of claim 1, wherein the conduit is an opening in a support structure.

26. A method comprising:

providing an expandable device, the expandable device comprising:

a sidewall formed of a plurality of interconnected structural members including spines and struts, the struts extending between the spines, wherein:

the spines include a spine having first and second end portions, each of the first and second end portions branching into a first leg and a second leg, the struts include a first strut, a second strut, a third strut, and a fourth strut, the first, second, third, and fourth struts being linear, wherein— the first strut having first and second end portions, wherein the first end portion of the first strut is connected to the first end portion of the third strut, the second strut having first and second end portions, wherein the second end portion of the second strut is connected to the second end portion of the fourth strut, the first leg of the first end portion of the spine is connected to the first strut between the first and second end portions of the first strut, the second leg of the first end portion of the spine is connected to the third strut between the first and second end portions of the third strut, the first leg of the second end portion of the spine is connected to the second strut between the first and second end portions of the second strut, and the second leg of the second end portion of the spine is connected to the fourth strut between the first and second end portions of the fourth strut;

increasing an arc length between circumferentially adjacent spines, thereby decreasing a longitudinal distance between the first end portions of longitudinally adjacent strut and increasing a circumferential distance between the second end portions of the longitudinally adjacent struts, wherein the first end portions of the longitudinally adjacent struts are coupled to a same one of the spines, and wherein the same one of the spines comprises a buckling region between the first end portions of the longitudinally adjacent struts;

longitudinally compressing the spines by decreasing the longitudinal distance between the first end portions of the longitudinally adjacent struts; and forcing the buckling regions of the spines to bow out of radial alignment with the struts and other regions of the spines, thereby forming arched protrusions along the sidewall of the expandable device.

27. The method of claim 26, further comprising positioning the expandable device in a conduit in a collapsed configuration, and wherein— when the expandable device is in the collapsed configuration, the spines and the struts together define a main lumen of the expandable device, and wherein the method further comprises (a) actuating an actuator within the main lumen to expand the expandable device within the conduit, thereby substantially blocking fluid flow through the main lumen of the expandable device, and (b) creating an annular lumen around the main lumen, thereby allowing fluid flow through the annular lumen while the actuator is blocking fluid flow through the main lumen.

28. The method of claim 26, wherein, when the expandable device is in a collapsed configuration, the spines and the struts together define a main lumen of the expandable device, wherein the method further comprises expanding an actuator within the main lumen to increase the circumferential arc length between adjacent spines.

29. The method of claim 26, further comprising creating an annular lumen between (a) portions of the arched protrusions that are radially farthest from the central longitudinal axis of the expandable device and (b) the struts and other regions of the spines.

30. The method of claim 26, wherein, when the expandable device is in a collapsed configuration, the spines and the struts are substantially the same radial distance from a central longitudinal axis of the expandable device and together define a main lumen of the expandable device.

31. The method of claim 26, wherein, when the expandable device is in the expanded configuration, (a) the struts and the other regions of the spines are a first radial distance from the central longitudinal axis, and (b) the buckling regions of the spines are a second radial distance from the central longitudinal axis different than the first radial distance.

32. The method of claim 26, wherein the expandable device is configured to be expanded within another expandable device.

* * * * *